United States Patent [19]

Bossert et al.

[11] 4,188,395
[45] Feb. 12, 1980

[54] 1,4-DIHYDROPYRIDINE DERIVATIVES SUBSTITUTED IN THE 2 POSITION, AND THEIR USE AS MEDICAMENTS

[75] Inventors: Friedrich Bossert, Wuppertal; Egbert Wehinger, Velbert; Horst Meyer, Wuppertal; Arend Heise, Wuppertal; Stanislav Kazda, Wuppertal; Kurt Stoepel, Wuppertal; Robertson Towart, Wuppertal; Wulf Vater, Leverkusen; Klaus Schlossmann, Wuppertal, all of Fed. Rep. of Germany

[73] Assignee: Bayer Aktiengesellschaft, Leverkusen, Fed. Rep. of Germany

[21] Appl. No.: 856,559

[22] Filed: Dec. 1, 1977

[30] Foreign Application Priority Data

Dec. 22, 1976 [DE] Fed. Rep. of Germany ....... 2658183

[51] Int. Cl.² .................... C07D 213/55; A61K 31/44
[52] U.S. Cl. .................... 424/266; 546/256; 546/257; 546/272; 546/284; 546/321
[58] Field of Search .................... 260/294.9, 294.8 G, 260/295.5 R, 295.5 B; 546/272, 284, 256, 257, 321; 424/266

[56] References Cited

U.S. PATENT DOCUMENTS 3,883,543  5/1975  Bossert .................... 260/295.5 B
3,974,278  8/1976  Bossert et al. .................... 260/295.5 R Primary Examiner—Alan L. Rotman
Attorney, Agent, or Firm—Sprung, Felfe, Horn, Lynch & Kramer

[57] ABSTRACT

The present invention provides 1,4-dihydropyridine derivatives of the formula in which

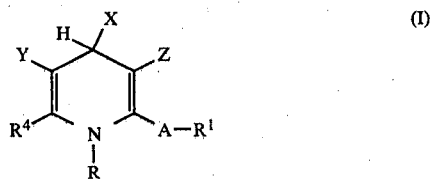

(I)

R represents hydrogen, alkyl, alkenyl, alkoxyalkyl, aryl or aralkyl, the alkyl and aryl groups being optionally substituted, A represents a straight-chain or branched alkylene radical, $R^1$ represents (a) an optionally substituted alkylthio group or (b) a group of the formula O—CO-alkyl, O—CO-aryl or O—CO-aralkyl, the alkyl and aryl groups being optionally substituted or (c) a phthalimido radical which is optionally substituted in the benzene ring, Y and Z are identical or different and each represents a group of the formula $COOR^2$ or $COR^2$, wherein $R^2$ represents alkyl, alkenyl, alkinyl, alkoxyalkyl, hydroxyalkyl, aminoalkyl, alkylaminoalkyl or aralkyl, the alkyl and aryl radicals being optionally substituted, or Y and Z are identical or different and each represents a cyano radical or a radical of the formula $S(O)_n$—$R^3$, wherein $R^3$ represents alkyl, alkenyl, alkoxyalkyl, aminoalkyl, alkylaminoalkyl, aryl or aralkyl, the alkyl and aryl radicals mentioned being optionally substituted, and n represents 0, 1 or 2, $R^4$ represents hydrogen or alkyl, the alkyl radical being optionally substituted or interrupted by oxygen, or represents the radical A—$R^1$, wherein A and $R^1$ have the abovementioned meaning, and X represents an aryl radical, which optionally contains one to three identical or different substituents selected from phenyl, alkyl, alkenyl, alkinyl, alkoxy, alkinoxy, acyloxy, halogen, trifluoromethyl, trifluoromethoxy, hydroxyl, nitro, cyano, azido, amino, alkylamino, acylamino, carbalkoxy, carboxamido, sulphonamide and $S(O)_n$-alkyl (n=0 to 2), or represents a quinolyl, pyridyl, pyrimidyl, thienyl, furyl or pyrryl radical which is optionally substituted by alkyl, alkylamino, nitro or halogen, or represents an optionally substituted aralkyl, cycloalkyl, cycloalkenyl or styryl radical, and acid addition salts thereof.

Also included in the invention are methods for the preparation of the 1,4-dihydropyridine derivatives of the invention, compositions containing said derivatives and methods for their use.

13 Claims, No Drawings

1,4-DIHYDROPYRIDINE DERIVATIVES SUBSTITUTED IN THE 2-POSITION, AND THEIR USE AS MEDICAMENTS

The present invention relates to new 1,4-dihydropyridine derivatives substituted in the 2-position, several processes for their preparation and their use as medicaments, in particular as agents which influence the circulation.

It has already been disclosed that 2,6-dimethyl-4-phenyl-1,4-dihydropyridine-3,5-dicarboxylic acid diethyl ester is obtained when benzylideneacetoacetic acid ethyl ester is reacted with B-amino-crotonic acid ethyl ester or acetoacetic acid ethyl ester and ammonia (Knoevenagel, Ber. dtsch. chem. Ges. 31, 743 (1898)). Furthermore, it is known that certain 1,4-dihydropyridines have interesting pharmacological properties (F. Bossert and W. Vater, Naturwissenschaften 58, 578 (1971)).

The present invention provides 1,4-dihydropyridine derivatives of the formula in which

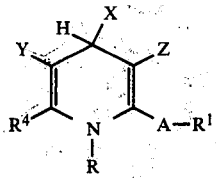   (I)

R represents hydrogen, alkyl, alkenyl, alkoxyalkyl, aryl or aralkyl, the alkyl and aryl groups being optionally substituted, A represents a straight-chain or branched alkylene radical, $R^1$ represents (a) an optionally substituted alkylthio group or (b) a group of the formula O—CO-alkyl, O—CO-aryl or O—CO-aralkyl, the alkyl and aryl groups being optionally substituted or (c) a phthalimido radical which is optionally substituted in the benzene ring, Y and Z are identical or different and each represents a group of the formula COOR$^2$ or COR$^2$, wherein $R^2$ represents alkyl, alkenyl, alkinyl, alkoxyalkyl, hydroxyalkyl, aminoalkyl, alkylaminoalkyl or aralkyl, the alkyl and aryl radicals being optionally substituted, or Y and Z are identical or different and each represents a cyano radical or a radical of the formula $S(O)_n$—$R^3$, wherein $R^3$ represents alkyl, alkenyl, alkoxyalkyl, aminoalkyl, alkylaminoalkyl, aryl or aralkyl, the alkyl and aryl radicals mentioned being optionally substituted, and n represents 0, 1 or 2, $R^4$ represents hydrogen or alkyl, the alkyl radical being optionally substituted or interrupted by oxygen, or represents the radical A—$R^1$, wherein A and $R^1$ have the abovementioned meaning, and X represents an aryl radical, which optionally contains one to three identical or different substituents selected from phenyl, alkyl, alkenyl, alkinyl, alkoxy, alkinoxy, acyloxy, halogen, trifluoromethyl, trifluoromethoxy, hydroxyl, nitro, cyano, azido, amino, alkylamino, acylamino, carbalkoxy, carboxamido, sulphonamido and $SO_n$-alkyl (n=0 to 2), or represents a quinolyl, pyridyl, pyrimidyl, thienyl, furyl or pyrryl radical which is optionally substituted by alkyl, alkylamino, nitro or halogen, or represents an optionally substituted aralkyl, cycloalkyl, cycloalkenyl or styryl radical, and acid addition salts thereof. The compounds of the invention (i.e. the compounds of the formula I and their acid addition salts) are pharmaceutically active. Of those compounds of the invention which are salts therefore, the pharmaceutically acceptable salts are most important and preferred.

It has also been found that the new 1,4-dihydropyridine derivatives, substituted in the 2-position, of the formula (I) are obtained when (A) keto compounds of the formula $$R^1\text{---}A\text{---}CO\text{---}CH_2\text{---}Z \qquad (II)$$

in which

A, $R^1$ and Z have the meaning indicated above, are reacted with amines of the formula $$H_2N\text{---}R \qquad (III)$$

in which

R has the meaning indicated above, or salts thereof, and, optionally after isolating the enamines formed from the keto compounds and amines, with ylidene derivatives of the formula

   (IV)

in which

X, Y and $R^4$ have the meaning indicated above, or (B) keto compounds of the formula $$R^4\text{---}CO\text{---}CH_2\text{---}Y \qquad (V)$$

in which $R^4$ and Y have the meaning indicated above, are reacted with amines of the formula III $$H_2N\text{---}R$$

or salts thereof, and, optionally after isolating the enamines formed herein, with ylidene derivatives of the formula $$X\text{---}CH\text{=}C\text{---}CO\text{---}A\text{---}R^1 \qquad (VI)$$

in which

A, X, $R^1$ and Z have the meaning indicated above, or (C) aldehydes of the formula $$X\text{---}CHO \qquad (VII)$$

in which

X has the meaning indicated above are reacted with a keto compound of the formula (II) or (V)

$$R^1\text{---}A\text{---}CO\text{---}CH_2\text{---}Z \qquad (II)$$

or

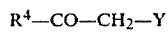 (V)

and with an enamine of the formulae (VIII) or (IX)

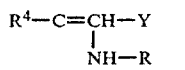 (VIII)

or

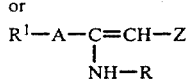 (IX)

in any desired combination, at least one of the two compounds reacted with the aldehyde carrying the grouping A—R$^1$.

In the reactions involving the combination of compounds of the formulae (II) and (IX) and in the combination of compounds of the formulae (V) and (VIII), only symmetric dihydropyridine esters are formed in each case.

A particular embodiment of variant C for the preparation of symmetric end products, that is to say of those end products in which R$^4$ has the meaning of A—R$^1$ and Y and Z are identical, consists in directly reacting two parts of a keto compound of the formula (II) or (V) with one part of an amine or amine salt of the formula (III) and with one part of an aldehyde of the formula (VII), without isolating the enamines formed during the reaction.

The salts are prepared in a manner which is in itself known by reacting the compounds obtained according to process variants A to C with suitable acids.

The 1,4-dihydropyridine derivatives, according to the invention, substituted in the 2-position exhibit significant pharmacological actions; in particular they are distinguished by a powerful vessel-influencing action. Because of their novel and versatile mode of action, the compounds according to the invention are an enrichment of pharmacy.

If 3-methoxybenzylidene-acetoacetic acid ethyl ester, y-phthalimido-acetoacetic acid methyl ester and methylamine (or the B-methylamino-y-phthalimido-crotonic acid methyl ester, which is formed here, directly) are used as the starting materials, the course of the reaction for variant (A) can be represented by the following equation:

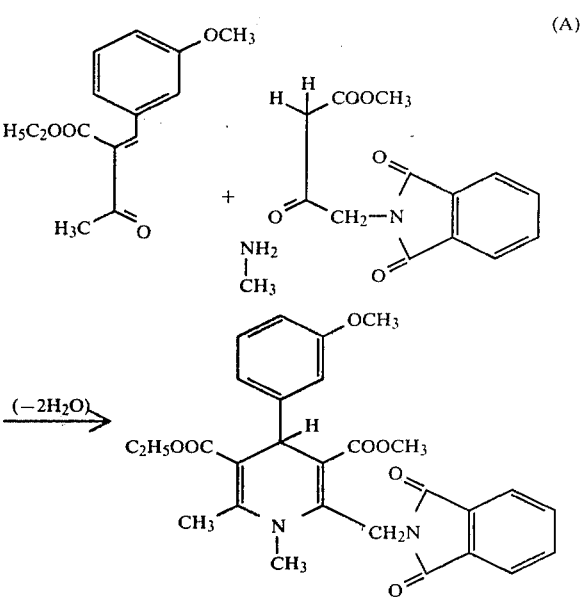

If 4-chlorobenzylindene-phthalimido-acetoacetic acid ethyl ester, acetoacetic acid ethyl ester and ammonia (or the -aminocrotonic acid ethyl ester, which is formed here and can be isolated, directly) are used as the starting components, the course of the reaction for variant (B) can be represented by the following equation:

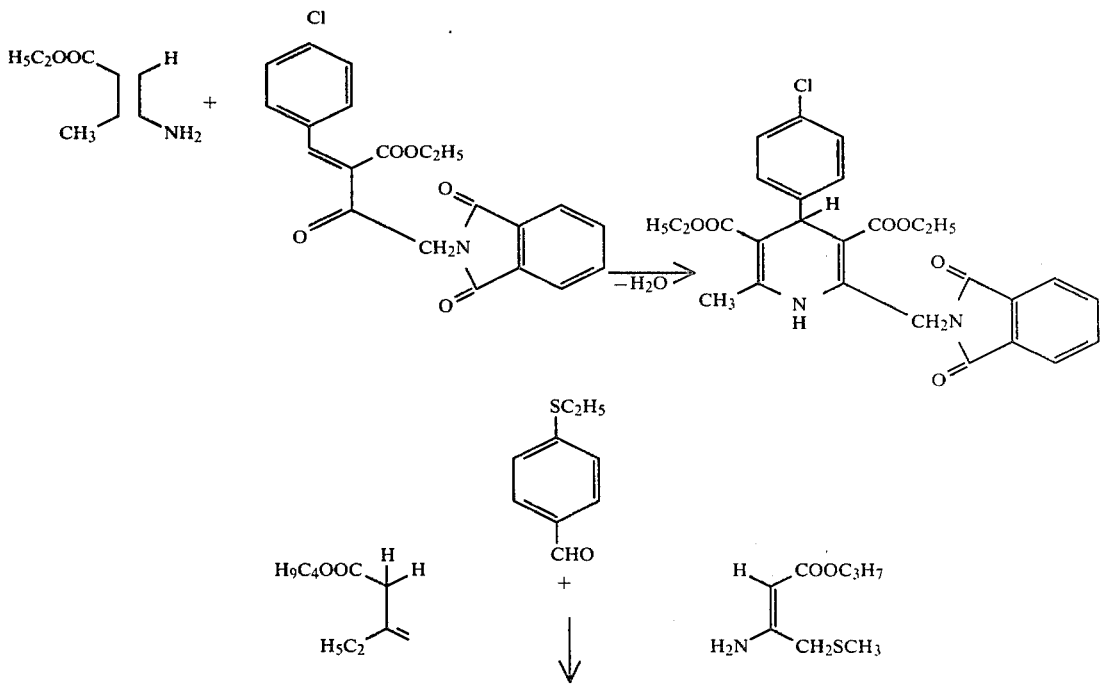

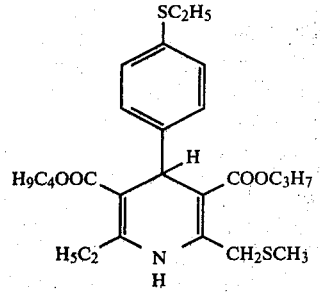

If 4-ethylthiobenzaldehyde, -amino-methylthiocrotonic acid propyl ester and propionylacetic acid butyl ester are used as the starting components, the course of the reaction for variant (C) can be represented by the following equation:

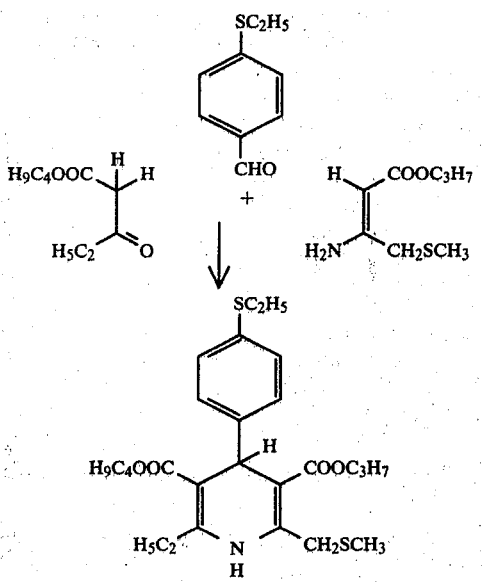

Some of the keto compounds of the formulae (II) and (V) and some of the corresponding enamines of the formulae (VIII) and (IX) are already known, or they can be prepared by processes which are known generally (compare B. Johnson and H. Chesnoff, J.A.C.S. 36, 1774 (1914); U.S. Pat. No. 2,351,366; and A. C. Cope, J.A.C.S. 67, 1017 (1945)).

Examples which may be mentioned are: β-dicarbonyl compounds: γ-methylmercaptoacetoacetic acid methyl ester, γ-methylthioacetoacetic acid ethyl ester, γ-methylmercaptoacetoacetic acid propyl ester, γ-methylmercaptoacetoacetic acid isopropyl ester, γ-methylmercaptoacetoacetic acid butyl ester, γ-ethylmercaptoacetoacetic acid methyl ester, γ-ethylmercaptoacetoacetic acid ethyl ester, γ-ethoxyacetoacetic acid propyl ester, γ-propylmercaptoacetoacetic acid ethyl ester, γ-propoxyacetoacetic acid isopropyl ester, γ-propylmercaptoacetoacetic acid tert.-butyl ester, γ-isopropylmercaptoacetoacetic acid methyl ester, γ-isopropoxyacetoacetic acid butyl ester, γ-butylmercaptoacetoacetic acid ethyl ester, γ-butylmercaptoacetoacetic acid isobutyl ester, γ-isobutylmercaptoacetoacetic acid propyl ester, γ-methylmercaptopropionylacetic acid methyl ester, γ-methoxypropionylacetic acid ethyl ester, γ-propylmercaptopropionylacetic acid propyl ester, γ-ethylmercaptopropionylacetic acid ethyl ester, γ-methylmercapto-γ-ethylpropionylacetic acid ethyl ester, 3,5-formylacetic acid ethyl ester, formylacetic acid butyl ester, acetoacetic acid methyl ester, acetoacetic acid ethyl ester, acetoacetic acid methyl ester, acetoacetic acid isopropyl ester, acetoacetic acid butyl ester, acetoacetic acid tert.-butyl ester, acetoacetic acid(α-hydroxyethyl)-ester or (β-hydroxyethyl)-ester, acetoacetic acid(α-methoxyethyl)-ester or (β-methoxyethyl)-ester, acetoacetic acid(α-ethoxyethyl)-ester or (β-ethoxyethyl)-ester, acetoacetic acid(α-n-propoxyethyl)-ester or (β-n-propoxyethyl)-ester, acetoacid acid allyl ester, acetoacetic acid propargyl ester, propionylacetic acid ethyl ester, butyrylacetic acid ethyl ester, isobutyrylacetic acid ethyl ester, oxaloacetic acid dimethyl ester, oxaloacetic acid diethyl ester, oxaloacetic acid isopropyl ester, acetonedicarboxylic acid dimethyl ester, acetonedicarboxylic acid diethyl ester, acetonedicarboxylic acid dibutyl ester, β-ketoadipic acid diethyl ester, γ-phthalimidoacetoacetic acid methyl ester, ethyl ester, propyl ester, isopropyl ester, butyl ester, isobutyl ester or tert.-butyl ester, (β-phthalimidopropionyl)-acetic acid methyl ester, ethyl ester, isopropyl ester, propyl ester or n-butyl ester, (α-phthalimidoisobutyryl)-acetic acid methyl ester, ethyl ester or propyl ester, (α-phthalimido-butyryl)-acetic acid methyl ester, ethyl ester, propyl ester, isopropyl ester or butyl ester, (β-phthalimido-butyryl)-acetic acid methyl ester, ethyl ester, propyl ester, isopropyl ester or butyl ester, (γ-phthalimidobutyryl)-acetic acid methyl ester, ethyl ester, propyl ester, isopropyl ester or butyl ester, γ-acetoxyacetoacetic acid methyl ester, γ-acetoxyacetoacetic acid ethyl ester, γ-acetoxyacetoacetic acid propyl ester, γ-acetoxyacetoacetic acid isopropyl ester, γ-acetoxyacetoacetic acid n-butyl ester, γ-acetoxyacetoacetic acid sec.-butyl ester, γ-acetoxyacetoacetic acid tert.-butyl ester, γ-acetoxy-propionylacetic acid methyl ester, δ-acetoxypropionylacetic acid ethyl ester, δ-acetoxypropionylacetic acid propyl ester, δ-acetoxypropionylacetic acid tert.-butyl ester, γ-propionyloxyacetoacetic acid methyl ester, γ-propionyloxyacetoacetic acid ethyl ester, γ-propionyloxyacetoacetic acid n-propyl ester, γ-butyryloxyacetoacetic acid methyl ester and γ-butyryloxyacetoacetic acid ethyl ester; and enaminecarboxylic acid esters: γ-methylmercapto-β-aminocrotonic acid methyl ester, γ-methoxy-β-aminocrotonic acid ethyl ester, γ-ethylmercapto-β-aminocrotonic acid propyl ester, γ-isopropylmercapto-β-methylaminocrotonic acid ethyl ester, γ-butylmercapto-γ-methyl-β-aminocrotonic acid ethyl ester, β-aminocrotonic acid methyl ester, β-aminocrotonic acid ethyl ester, β-aminocrotonic acid isopropyl ester, β-aminocrotonic acid butyl ester, β-aminocrotonic acid (α-methoxyethyl)-ester or (β-methoxyethyl)-ester, β-aminocrotonic acid β-ethoxyethyl ester, β-aminocrotonic acid β-propoxyethyl ester, β-aminocrotonic acid t-butyl ester, β-aminocrotonic acid cyclohexyl ester, β-amino-β-ethyl-acrylic acid ethyl ester, iminosuccinic acid dimethyl ester, iminosuccinic acid diethyl ester; iminosuccinic acid dipropyl ester, iminosuccinic acid dibutyl ester, β-iminoglutaric acid dimethyl ester, β-iminoglutaric acid diethyl ester, β-iminoadipic acid dimethyl ester, β-iminoadipic acid diisopropyl ester, β-methylaminocrotonic acid methyl ester, β-ethylaminocrotonic acid ethyl ester, β-methyliminoglutaric acid diethyl ester, β-amino-γ-phthalimidocrotonic acid methyl ester, β-amino-γ-phthalimidocrotonic acid ethyl ester, β-amino-γ-phthalimidocrotonic acid propyl ester, β-amino-γ-phthalimidocrotonic acid isopropyl ester, 3-amino-γ-phthalimidocrotonic acid butyl ester, 3-amino-γ-phthalimidoethylcrotonic acid ethyl ester, β-methylamino-γ-phthalimidocrotonic acid ethyl ester, β-ethylamino-γ-phthalimidocrotonic acid propyl ester, β-amino-γ-acetoxycrotonic acid methyl ester, β-amino-γ-acetoxycrotonic acid ethyl ester, β-amino-γ-acetoxycrotonic acid propyl ester, β-amino-γ-acetoxycrotonic acid isopropyl ester, ζ-amino-γ-acetoxycrotonic acid butyl ester, ζ-amino-γ-acetoxycrotonic acid ethyl ester, β-methylamino-γ-acetoxycrotonic acid ethyl ester and β-ethylamino-γ-acetoxycrotonic acid propyl ester.

The aldehydes of the formula (VII) which can be used according to the invention are already known or can be prepared by known methods (E. Mosettic, Org. Reactions, VIII, 218 et seq., (1954)).

Examples which may be mentioned are: Aldehydes: benzaldehyde, 2-, 3- or 4-methoxybenzaldehyde, 2-isopropxybenzaldehyde, 3-butoxybenzaldehyde, 3,4-dioxymethylenebenzaldehyde, 3,4,5-trimethoxy-benzaldehyde, 2-, 3- or 4-chlorobenzaldehyde, 2-, 3- or 4-bromobenzaldehyde, 2-, 3- or 4-iorobenzaldehyde or 2-, 3- or 4-fluorobenzaldehyde, 2,4- or 2,6-dichlorobenzaldehyde, 2,4-dimethylbenzaldehyde, 3,5-diisopropyl-4-methoxybenzaldehyde, 2-, 3- or 4-nitrobenzaldehyde, 2,4- or 2,6-dinitrobenzaldehyde, 2-nitro-6-bromobenzaldehyde, 2-nitro-3-methoxy-6-chlorobenzaldehyde, 2-nitro-4-chlorobenzaldehyde, 2-nitro-4-methoxybenzaldehyde, 2-, 3- or 4-trifluoromethylbenzaldehyde, 2-, 3- or 4-dimethylaminobenzaldehyde, 4-dibutylaminobenzaldehyde, 4-acetaminobenzaldehyde, 2-, 3- or 4-cyanobenzaldehyde, 2-nitro-4-cyanobenzaldehyde, 3-chloro-4-cyanobenzaldehyde, 2-, 3- or 4-methylmercaptobenzaldehyde, 2-methylmercapto-5-nitrobenzaldehyde, 2-butylmercaptobenzaldehyde, 2-, 3- or 4-methylsulphinylbenzaldehyde, 2-, 3- or 4-methylsulphonylbenzaldehyde, benzaldehyde-2-carboxylic acid ethyl ester, benzaldehyde-3-carboxylic acid isopropyl ester, benzaldehyde-4-carboxylic acid butyl ester, 3-nitrobenzaldehyde-4-carboxylic acid ethyl ester, cinnamaldehyde, hydrocinnamalde hyde, formylcyclohexane, 1-formylcyclohex-3-ene, 1-formylcyclohex-1,3-ine, 1-formylcyclopent-3-ene, ζ,α-, β- or γ-pyridinealdehyde, 6-methylpyridine-2-aldehyde, furane-2-aldehyde, thiophene-2-aldehyde and pyrrole-2-aldehyde, N-methylpyrrole-2-aldehyde, 2-, 3- or 4-azidobenzaldehyde, pyrimidine-4-aldehyde, 5-nitro-6-methylpyridine-2-aldehyde, 1- or 2-naphthaldehyde, 5-bromo-1-naphthaldehyde, quinoline-2-aldehyde, 7-methoxy-quinoline-4-aldehyde and isoquiniine-1-aldehyde.

Some of the ylidene derivatives of the formulae (IV) and (VI) which can be used according to the invention are known, or they can be prepared by methods which are known generally (Org. Reactions XI, 204 et seq., (1967)).

Examples which may be mentioned are: Ylidene-β-ketocarboxylic acid esters: benzylidene-γ-methoxyacetoacetic acid ethyl ester, 2'-nitrobenzylidene-γ-methylmercaptoacetoacetic acid ethyl ester, 3'-methoxybenzylidene-γ-ethylmercaptoacetoacetic acid methyl ester, 3',4'-dimethoxybenzylidene-γ-propoxyacetoacetic acid propyl ester 2'-trifluoromethylbenzylidene-γ-methylmercaptoacetoacetic acid ethyl ester, 2-chlorobenzylidene-γ-ethoxyacetoacetic acid propyl ester, 3-mercaptobenzylidene-γ-butylmercaptoacetoacetic acid ethyl ester, benzylideneacetoacetic acid methyl ester, 2'-nitrobenzlidene-acetoacetic acid methyl ester, 3'-nitrobenzylideneacetoacetic acid propargyl ester, 3'-nitrobenzylideneacetoacetic acid allyl ester, 3'-nitrobenzylideneacetoacetic acid ethoxyethyl ester, 4'-nitrobenzylideneacetoacetic acid isopropyl ester, 3'-nitro-6'chlorobenzlideneacetoacetic acid methyl ester, 2'-cyanobenzylidenepropionylacetic acid ethyl ester, 3'-cyanobenzylideneacetoacetic acid methyl ester, 3'-nitro-4'-chlorobenzylideneacetoacetic acid tert.-butyl ester, 2'-nitro-4'-methoxybenzylideneacetoacetic acid methyl ester, 2'-cyano-4'-methylbenzylideneacetoacetic acid ethyl ester, 2'-azidobenzylideneacetoacetic acid ethyl ester, 2'-methylmercaptobenzylideneacetoacetic acid isopropyl ester, 2'-sulphinylmethylbenzylideneacetoacetic acid ethyl ester, 2-sulphonylmethylacetoacetic acid ethyl ester, 2'-4'-nitrobenzylideneoxaloacetic acid diethyl ester, 2'-4'-dihydroxymethylenebenzylideneoxaloacetic acid dimethyl ester, 3'-ethoxybenzylidene-β-ketoglutaric acid diethyl ester, (2'-ethoxy-1'-naphthylidene)-acetoacetic acid methyl ester, (1'-isoquinolyl)-methylideneacetoacetic acid methyl ester, α-pyridylmethylideneacetoacetic acid methyl ester, α-pyridylmethylideneacetoacetic acid allyl ester, α-pyridylmethylideneacetoacetic acid cyclohexyl ester, α-pyridylmethylideneacetoacetic acid β-methoxyethyl ester, 6-methyl-α-pyridylmethylideneacetoacetic acid ethyl ester, 4',6'-dimethoxy(5'-pyrimidyl)-methylideneacetoacetic acid ethyl ester, (2'-thenyl)-methylideneacetoacetic acid ethyl ester, (2'-furyl)methylideneacetoacetic acid allyl ester, (2'-pyrryl)-methylideneacetoacetic acid methyl ester, α-pyridylmethylidenepropionylacetic acid methyl ester, 2'-, 3'- or 4'methoxybenzylideneacetoacetic acid ethyl ester, 2'-methoxybenzylideneacetoacetic acid propargyl ester, 2'-isopropoxybenzylideneacetoacetic acid ethyl ester, 3'-butoxybenzylideneacetoacetic acid methyl ester, 3',4',5'-trimethoxybenzylideneacetoacetic acid allyl ester, 2'-methyl-benzylidenepropionylacetic acid methyl ester, 2'-methylbenzylideneacetoacetic acid β-propoxyethyl ester, 3',4'-dimethoxy-5'-bromobenzylideneacetoacetic acid ethyl ester, 2'-, 3'- or 4'-chlorobenzylideneacetoacetic acid ethyl ester, 2'-, 3'- or 4'-bromobenzylideneacetoacetic acid ethyl ester, 2'-, 3'- or 4'-fluorobenzylideneacetoacetic acid ethyl ester or 2'-, 3' or 4'-iodobenzylideneacetoacetic acid ethyl ester, 3'-chlorobenzylidenepropionylacetic acid ethyl ester, 2'-, 3' or 4'-trifluoromethylbenzylideneacetoacetic acid propyl ester, 2'-carboethoxybenzylideneacetoacetic acid ethyl ester, 4-carboxyisopropylbenzylideneacetoacetic acid isopropyl ester, benzylidene-γ-ethylmercapto-acetoacetic acid methyl ester, 2'-nitrobenzylidene-γ-propylmercapto-acetoacetic acid methyl ester, 3'-nitrobenzylidene-γ-methylmercapto-acetoacetic acid methyl ester, 3'-nitro-benzylideneacetoacetic acid propyl ester 4'-nitrobenzylidene-γ-methylmercapto-acetoacetic acid isopropyl ester, 3'-nitro-6-chlorobenzylidene-γ-isopropylmercapto-acetoacetic acid methyl ester, 2'-cyanobenzylidene-γ-butylmercapto-acetoacetic acid methyl ester, 2'-cyanobenzylidene-γ-ethylmercaptopropionylacetic acid ethyl ester, 2'-nitro-4'-methoxybenzylidene-γ-propylmercapto-acetoacetic acid methyl ester, 2'-azidobenzylidene-γ-methylmercaptoacetoacetic acid ethyl ester, 2'-methylmercaptobenzylidene-γ-ethylmercaptoacetoacetic acid methyl ester, 3'-methylmercaptobenzylidene-γ-methylmercaptoacetoacetic acid isopropyl ester, 2'-sulphinylmethylbenzylidene-methylmercapto-acetoacetic acid ethyl ester, 2'-sulphonylmethyl-γ-methylmercaptoacetoacetic acid ethyl ester, (2'-ethoyl-1'-naphthylidene)-γ-methylmercapto-acetoacetic acid methyl ester, (1'-isoquinolyl)-methylidene-γ-ethylmercapto-acetoacetic acid methyl ester, α-pyridylmethylidene-γ-propylmercapto-acetoacetic acid ethyl ester, 4',6'-dimethyl-(5'-pyrimidyl)-methylidene-γ-methylmercapto-acetoacetic acid ethyl ester, (2'-thenyl)-γ-methylmercapto-methylideneacetoacetic acid ethyl ester, (2'-furyl)-γ-ethylmercapto-methylideneacetoacetic acid butyl ester, 2'-, 3'- or 4'-methoxybenzylidene-γ-methylmercaptoacetoacetic acid ethyl ester, 2'-isopropoxybenzylidene-γ-isopropyl-mercaptoacetoacetic acid ethyl ester, 3'-butoxybenzylidene-γ-methylmercaptoacetoacetic acid methyl ester, 3',4',5'-trimethoxy-benzylidene-γ-propylmercapto-acetoacetic acid propyl ester, 2'-methylbenzylidene-γ-methylmercaptopropionylacetic acid methyl ester, 2'-, 3'- or 4'-trifluoromethylbenzylidene-γ-methylmercapto-acetoacetic acid propyl ester 2'-trifluoromethylbenzylidene-γ-methylmercapto-acetoacetic acid isopropyl ester, 3'-trifluoromethyl-benzylidene-γ-ethylmercaptoacetoacetic acid methyl ester, 2'-carbothoxybenzylidene-γ-methylmercapto-acetoacetic acid ethyl ester, 3'-carboxymethylbenzylidene-γ-ethylmercapto-acetoacetic acid methyl ester, 4-carboxyisopropylbenzylidene-γ-propylmercapto-acetoacetic acid isopropyl ester, benzylidene-γ-phthalimidoacetoacetic acid ethyl ester, 2-nitrobenzylidene-γ-phthalimidoacetoacetic acid methyl ester, 2-trifluoromethylbenzylidene-γ-phthalimidoacetoacetic acid ethyl ester, 3-nitrobenzylidene-γ-phthalimidoacetoacetic acid propyl ester, 3-methoxybenzylidene-γ-phthalimidoacetoacetic acid isopropyl ester, 2-methylmercaptobenzylidene-γ-phthalimidoacetoacetic acid butyl ester, 3-fluorobenzylidene-γ-phthalimidoacetoacetic acid ethyl ester, benzylidene-γ-acetoxyacetoacetic acid propyl ester, 3-nitrobenzylidene-γ-propionyloxyacetoacetic acid propyl ester, 2-trifluorobenzylidene-γ-acetoxyacetoacetic acid β-methoxyethyl ester, 2-nitrobenzylidene-γ-acetoxypropionylacetic acid methyl ester, α-pyridylmethylidene-γ-acetoxyacetoacetic acid ethyl ester, 2-nitrobenzylidene-δ-acetoxypropionylacetic acid butyl ester and 2-chlorobenzylidene-γ-acetoxyacetoacetic acid benzyl ester.

The amines of the formula (III) which can be used according to the invention are already known.

Examples which may be mentioned are: ammonia, monoalkylamines, such as methylamine, ethylamine, propylamine, butylamine, isopropylamine, isobutylamine; monoalkenylamines, such as allylamine, aralkyl amines, such as benzylamine, p-chlorobenzylamine; alkoxyalkyl amines, such as β-methoxy-ethylamine and arylamines, such as p-chloroaniline.

Unless expressly defined otherwise, in the present application the term optionally substituted alkyl represents straight-chain or branched alkyl with preferably 1 to 6, in particular 1 to 4, carbon atoms. Examples which may be mentioned are optionally substituted methyl, ethyl, n-propyl, iso-propyl, n-butyl, iso-butyl and tert.-butyl.

Optionally substituted alkenyl is straight-chain or branched alkenyl with preferably 2 to 6, in particular 2 to 4, carbon atoms. Examples which may be mentioned are optionally substituted ethenyl, propen-1-yl, propen-2-yl and buten-3-yl.

Optionally substituted alkinyl is straight-chain or branched alkinyl with preferably 2 to 6, in particular 2 to 4, carbon atoms. Examples which may be mentioned are optionally substituted ethinyl, propin-1-yl, propin-2-yl and butin-3-yl.

Optionally substituted aryl which may be mentioned are, preferably, optionally substituted phenyl or naphthyl.

Optionally substituted aralkyl is aralkyl with preferably 6 or 10, in particular 6, carbon atoms in the aryl part and preferably 1 to 4, in particular 1 to 2, carbon atoms in the alkyl part, the aryl part and/or the alkyl part being optionally substituted. Examples which may be mentioned are optionally substituted benzyl and phenethyl.

Halogen atoms are preferably fluorine, chlorine, bromine and iodine, in particular fluorine and chlorine.

Alkylamino preferably represents monoalkylamino or dialkylamino with 1 to 4, in particular 1 or 4, carbon atoms in the alkyl part in each case. Examples which may be mentioned are monomethylamino, N,N-dimethylamino, methyl-ethylamino, methyl-benzylamino and n-butylamino. The carbalkoxy radicals mentioned preferably contain 2 to 4, in particular 2 or 3, carbon atoms. Examples which may be mentioned are carbomethoxy and carboethoxy.

The alkoxyalkyl substituents mentioned preferably contain 1 or 2 carbon atoms in the alkyl part and 1 to 3 carbon atoms in the alkoxy part. Examples which may be mentioned are methoxyethyl, ethoxymethyl and propoxyethyl.

Dihydropyridine derivatives of the formula I in which

R represents hydrogen, alkyl with 1 to 4 carbon atoms, in particular methyl or ethyl, or represents benzyl, A represents a straight-chain or branched alkylene radical with 1 to 6 carbon atoms, in particular with 1 to 4 carbon atoms, $R^1$ represents (a) an alkylmercapto group with 1 to 4 carbon atoms or (b) the group O—CO-alkyl with 1 to 4 carbon atoms in the alkyl group or O—CO-benzyl or (c) a phthalimido radical, Y and Z individually represent the groups $COOR^2$ or $COR^2$ wherein $R^2$ represents alkyl, alkenyl, alkinyl, alkoxyalkyl, hydroxyalkyl, alkylmercaptoalkyl, aminoalkyl, monoalkylaminoalkyl or dialkylaminoalkyl, the alkyl groups mentioned containing preferably 1 to 6 carbon atoms, in particular 1 to 4 carbon atoms, and the alkenyl and alkinyl groups mentioned preferably containing 2 to 4 carbon atoms, or represents phenyl or benzyl, or Y and Z represent a cyano radical or the radical $S(O)_n$—$R^3$, wherein $R^3$ represents alkyl, alkenyl, aminoalkyl, alkylaminoalkyl with up to 4 C atoms in each case, phenyl, naphthyl or benzyl, the abovementioned radicals being optionally substituted, and n represents 0 or 2, $R^4$ represents hydrogen, alkyl or alkoxyalkyl with 1 to 4 carbon atoms, or represents the radical A—$R^1$, wherein A and $R^1$ have the abovementioned meaning, and X represents a phenyl radical which is optionally substituted by one or two identical or different substituents from the group nitro, halogen, trifluoromethyl, cyano, phenyl, trifluoromethoxy, amino, alkylamino, alkyl, alkoxy or alkylmercapto with 1 or 2 carbon atoms in the alkyl radical in each case, or represents a naphthyl, pyridyl, pyrimidyl, thienyl, cycloalkenyl or benzyl radical which is optionally substituted by nitro or halogen.

are of particular interest.

The salts, according to the invention, of the 1,4-dihydripyridine derivatives are prepared by methods which are known generally, for example by dissolving the base in ether and adding suitable acids to the solution.

Examples which may be mentioned of inorganic and organic acids which form physiologically acceptable acid addition salts with the dihydropyridines of the formula (I) are: hydrogen halide acids, such as hydrochloric acid and hydrobromic acid, in particular hydrochloric acid, phosphoric acids, sulphuric acid, nitric acid, monofunctional and bifunctional carboxylic acids and hydroxycarboxylic acids, such as acetic acid, maleic acid, succinic acid, fumaric acid, tartaric acid, citric acid, salicylic acid, sorbic acid, lactic acid and 1,5-naphthalenedicarboxylic acid, and naphthalenedisulphonic acid.

Water and all inert organic solvents can be used as the dilutent in process variants (A) to (C). These include, preferably, alcohols, for example lower alkyl alcohols with preferably 1 to 4 carbon atoms, such as ethanol, methanol and isopropanol, ethers, for example lower dialkyl ethers (preferably 3 to 5 carbon atoms), such as diethyl ether, or cyclic ethers, such as tetrahydrofurane and dioxane, lower aliphatic carboxylic acids (preferably 2 to 5 carbon atoms), such as acetic acid and propionic acid, lower dialkylformamides (preferably 1 or 2 carbon atoms per alkyl group, such as dimethylformamide, lower alkylnitriles (preferably 2 to 4 carbon atoms), such as acetonitrile, dimethylsulphoxide, liquid heteroaromatic bases, such as pyridine, and mixtures of these solvents, including water, with one another.

The reaction temperatures in process variants (A) to (C) can be varied within a relatively wide range. In general, the reaction is carried out between about 20° and about 150° C., preferably between 50° and 100° C. and in particular at the boiling point of the solvent used.

The reaction can be carried out under normal pressure, but also under elevated pressure. In general, the reaction is carried out under normal pressure.

In carrying out process variants (A) to (C) according to the invention, the starting materials participating in the reaction are preferably each employed in approximately molar amounts. The amine used, or salt thereof, is appropriately added in an excess of 1 to 2 mols. The molar ratio can be varied over a wide range without adversely influencing the result.

In detail, new active compounds which may be mentioned in addition to the compounds described in the examples are: 2-β-methylmercaptoethyl-6-ethyl-4-(2-chlorophenyl)-1, 4-dihydropyridine-3-carboxylic acid methyl ester 5-carboxylic acid benzyl ester, 2-isopropylmercaptomethyl-6-methyl-4-(2-methoxyphenyl)-1,4-dihydropyridine-3,5-dicarboxylic acid diisopropyl ester, 2,6-di-(β-ethylmercaptoethyl)-4-(2-methoxy-4-bromophenyl)-1,4-dihydropyridine-3-carboxylic acid methyl ester 5-carboxylic acid propyl ester, 2-propionyloxyethyl-6-propyl-5-(2-trifluoromethylphenyl)-1,4-dihydropyridine-3-carboxylic acid ethyl ester 5-carboxylic acid methyl ester, 2,6-di-(β-ethoxyethyl)-4-(3-nitrophenyl)-1,4-dihydropyridine-3,5-dicarboxylic acid dimethyl ester, 2,6-dipropionyloxymethyl-4-(γ-pyridyl)-1,4-dihydropyridine-3,5-dicarboxylic acid diisopropyl ester, 2-(β-phthalimidoethyl)-6-isopropyl-4-phenyl-1,4-dihydropyridine-3-carboxylic acid methyl ester 5-carboxylic acid allyl ester, 2-(γ-phthalimidopropyl)-6-ethyl-4-(3,4,5-trimethoxyphenyl)-1,4-dihydropyridine-3,5-dicarboxylic acid dipropyl ester, 2,6-(γ-diphthalimido-n-propyl)-4-(2-methylmercaptophenyl)-1,4-dihydropyridine-3-carboxylic acid propyl ester 5-carboxylic acid (β-methoxethyl ester), 2-methylthiomethyl-6-methyl-4-(2-nitrophenyl)-5-methylsulphonyl-1,4-dihydropyridine-3-carboxylic acid methyl ester, 2-(β-phthalimidoethyl)-6-methyl-4-(3-nitrophenyl)-5-phenylsulphonyl-1,4-dihydropyridine-3-carboxylic acid ethyl ester, 2-acetoxymethyl-6-methyl-4-(2-chlorophenyl)-5-phenylsulphonyl-1,4-dihydropyridine-3-carboxylic acid butyl ester, 2-propionyloxymethyl-6-ethyl-4-(2-methoxyphenyl)-5-benzylsulphonyl-1,4-dihydropyridine-3-carboxylic acid ethyl ester and 2-(γ-phthalimidopropyl)-6-methyl-4-(2-trifluoromethylphenyl)-5-phenylsulphonyl-1,4-dihydropyridine-3-carboxylic acid isopropyl ester.

The new compounds can be used as medicaments, in particular as active compounds influencing the vessels and circulation.

The compounds according to the invention have a broad and diverse spectrum of pharmacological activity.

In detail, the compounds according to the invention have the following main actions:

1. On parenteral, oral and perlingual administration the new compounds produce a distinct and long-lasting dilation of the coronary vessels.

This action on the coronary vessels is intensified by a simultaneous nitrite-like effect of reducing the load on the heart. They influence or modify the heart metabolism in the sense of an energy saving.

2. The new compounds lower the blood pressure of normotonic and hypertonic animals and can thus be used as antihypertensive agents.

3. The excitability of the stimulus formation and excitation conduction system within the heart is lowered, so that an anti-fibrillation action which can be demonstrated at therapeutic doses results.

4. The tone of the smooth muscle of the vessels is greatly reduced under the action of the compounds. This vascular-spasmolytic action can take place in the entire vascular system or can manifest itself more or less isolated in circumscribed vascular regions (such as, for example, the central nervous system).

5. The compounds have strongly muscular-spasmolytic actions which manifest themselves on the smooth muscle of the stomach, the intestinal tract, the urogenital tract and the respiratory system.

6. The compounds influence the cholesterol level and lipid level of the blood.

The new compounds are accordingly suitable for preventing, ameliorating or curing diseases, for which, in particular, the effects indicated above are desired.

The present invention provides a pharmaceutical composition containing as active ingredient a compound of the invention in admixture with a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile or isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or sub-multiple (down to a fortieth) of a daily dose of the compound of the invention in association with a carrier and/or enclosed within an envelope. Whether the medicament contains a daily dose or, for example, a half, a third, or a quarter of a daily dose will depend on whether the medicament is to be administered once or, for example, twice, three times or four times a day respectively.

The pharmaceutical compositions according to the invention may, for example, take the form of ointments, gels, pastes, creams, sprays (including aerosols), lotions, suspensions, solutions and emulsions of the active ingredient in aqueous or non-aqueous diluents, syrups, granulates or powders.

The diluents to be used in pharmaceutical compositions (e.g., granulates) adapted to be formed into tablets, dragees, capsules and pills include the following:

(a) fillers and extenders, e.g., starch, sugars, mannitol, and silicic acid; (b) binding agents, e.g., carboxymethyl cellulose and other cellulose derivatives, alginates, gelatine and polyvinyl pyrrolidone; (c) moisturizing agents, e.g., glycerol; (d) disintegrating agents, e.g., agar-agar, calcium carbonate and sodium bicarbonate; (e) agents for retarding dissolution, e.g., paraffin; (f) resorption accelerators, e.g., quaternary ammonium compounds; (g) surface active agents, e.g., cetyl alcohol, glycerol monostearate; (h) adsorptive carriers, e.g., kaolin and bentonite; (i) lubricants, e.g., talc, calcium and magnesium stearate and solid polyethylene glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents.

The diluents to be used in pharmaceutical compositions adapted to be formed into suppositories can, for example, be the usual water-soluble or water-insoluble diluents, such as polyethylene glycols and fats (e.g., cocoa oil and high esters [e.g., $C_{14}$-alcohol with $C_{16}$-fatty acid]) or mixtures of these diluents.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and amulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils (for example ground nut oil), glycerol, tetrahydrofurfuryl alcohol, polyethylene glycols and fatty acid esters of sorbitol or mixtures thereof.

For parenteral administration, the solutions and emulsions should be sterile, and, if appropriate, blood-isotonic.

The pharmaceutical compositions which are suspensions can contain the usual diluents, such as liquid diluents, e.g., water, ethyl alcohol, propylene glycol, surface-active agents (e.g., ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention can also contain colouring agents and preservatives as well as perfumes and flavouring additions (e.g., peppermint oil and eucalyptus oil) and sweetening agents (e.g., saccharin).

The pharmaceutical compositions according to the invention generally contain from 0.1 to 99.5, usually from 0.5 to 95% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted, by virtue of their shape or packaging, for medical administration and may be, for example, any of the following: tablets, (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The preferred daily dose for administration of the medicaments of the invention is 0.5 mg to 10 g of active ingredient.

The production of the above-mentioned pharmaceutical compositions and medicaments is carried out by any method known in the art, for example, by mixing the active ingredient(s) with the diluent(s) to form a pharmaceutical composition (e.g., a granulate) and then forming the composition into the medicament (e.g., tablets).

This invention further provides a method of combating (including prevention, relief and cure of) the above-mentioned diseases in warm-blooded animals, which comprises administering to the animals a compound of the invention alone or in admixture with a diluent or in the form of a medicament according to the invention.

It is envisaged that these active compounds will be administered perorally, parenterally (for example, intramuscularly, intraperitoneally or intravenously), rectally or locally, preferably perorally or parenterally, especially intravenously. Preferred pharmaceutical compositions and medicaments are therefore those adapted for oral or intravenous administration.

In general it has proved advantageous to administer the active compound or compounds in amounts of about 0.01 to about 50, preferably 0.1 to 5, mg/kg of body weight every 24 hours, in the case of parenteral (intravenous) administration, and in amounts of about 0.1 to about 100, preferably 1 to 30, mg/kg of body weight every 24 hours, in the case of oral administration, optionally in the form of several individual administrations, in order to achieve the desired results. An individual administration preferably contains the active compound or compounds in amounts of about 0.005 to 50, in particular 0.5 to 20, mg/kg of body weight. However, it can be necessary to deviate from the dosages mentioned, and in particular to do so as a function of the nature and body weight of the subject to be treated, the nature and the severity of the illness, the nature of the formulation and of the administration of the medicament, and the time or interval over which the administration takes place. Thus it can be sufficient in some cases to manage with less than the above-mentioned amount of active compound, whilst in other cases the above-mentioned amount of active compound must be exceeded. The particular optimum dosage required and the type of administration of the active compounds can be easily ascertained by anyone skilled in the art, on the basis of his expert knowledge.

The following Examples illustrate the preparation of individual compounds of the sections.

EXAMPLE 1

2-Methylmercaptomethyl-6-methyl-4-
-pyridyl-1,4-dihydropyridine-3,5-dicarboxylic acid
diethyl ester

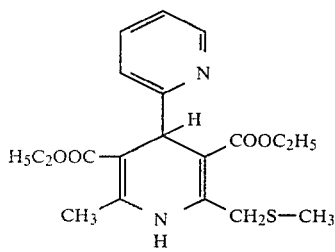

10.70 g of pyridine-2-aldehyde, 17.86 g of γ-methylmercaptoacetoacetic acid ethyl ester and 61.3 g of β-aminocrotonic acid ethyl ester are heated to the boil overnight in 80 ccs of ethanol. After cooling, the mixture is filtered and the residue is recrystallised from ethanol.

Beige crystals of melting point 136° C., yield: 50%.

EXAMPLE 2

2-Methylmercaptomethyl-6-methyl-4-(2'-nitrophenyl)-
1,4-dihydropyridine-3-carboxylic acid ethyl ester
5-carboxylic acid n-propyl ester

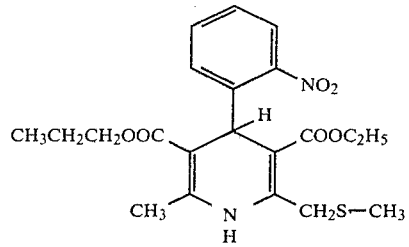

15 g of 2-nitrobenzaldehyde, 17.6 g of γ-methylmercaptoacetoacetic acid ethyl ester and 14.2 g of γ-aminocrotonic acid n-propyl ester (boiling point 107°–112°) in 100 ccs of dioxane are heated under reflux overnight, the mixture is cooled and the precipitate is filtered off and rinsed with cold ether.

Yellow crystals of melting point 135° C., yield: 40%.

EXAMPLE 3

2-Mercaptomethyl-6-methyl-4-(2'-trifluoromethyl-
phenyl)-1,4-dihydropyridine-3-carboxylic acid ethyl
ester 5-carboxylic acid methyl ester

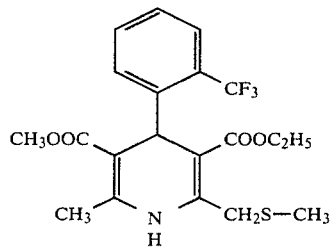

17.4 of 2-trifluoromethylbenzaldehyde, 17.6 g of γ-methylmercaptoacetoacetic acid ethyl ester and 11.6 g of β-aminocrotonic acid methyl ester in 80 ccs of ethanol are heated under reflux overnight and the mixture is then evaporated in vacuo.

Yellow oil $n_D^{50} = 1.5300$, yield: 85%

EXAMPLE 4

2-Methylmercapto-6-methyl-4-(2'-methylmercapto-
phenyl)-1,4-dihydropyridine-3-carboxylic acid ethyl
ester 5-carboxylic acid methyl ester

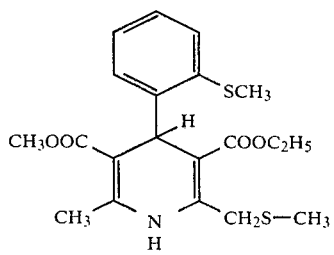

15.2 g of 2-methylmercaptobenzaldehyde, 17.6 g of γ-methylmercaptoacetoacetic acid ethyl ester and 14.2 g. of γ-aminocrotonic acid n-methyl ester in 80 ccs of ethanol are heated under reflux overnight, the mixture is cooled and the precipitate is filtered off and recrystallised from ethanol.

Yellow crystals of melting point 128°–130° C., yield: 45%

EXAMPLE 5

1-Methyl-2,6-(dimethylmercaptomethyl)-4-(2'-nitrophenyl)-1,4-dihydropyridine-3,5-dicarboxylic acid diethyl ester

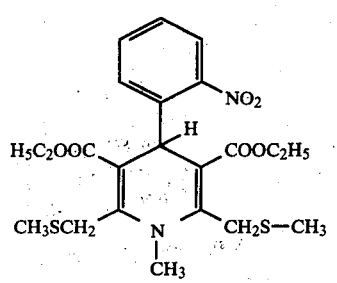

A solution of 7.5 g of 2-nitrobenzaldehyde, 17.6 g of γ-methylmercaptoacetoacetic acid ethyl ester and 4 g of methylamine chlorohydrate in 30 ccs of pyridine is heated to 90°–100° C. for 7 hours and poured into ice water, the aqueous phase is decanted off and the oil is taken up in ether. The ether solution is then washed until free from pyridine, dried over sodium sulphate and evaporated.

Oil, yield: 90%

EXAMPLE 6

2,6-Dimethylmercaptomethyl-4-(3'-nitrophenyl)-,4-dihydropyridine-3,5-dicarboxylic acid diethyl ester

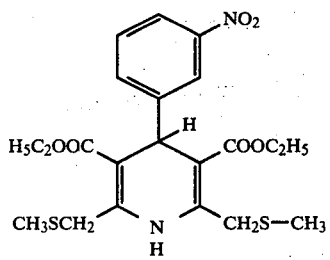

7.5 g of 3-nitrobenzaldehyde, 8.8 g of γ-methylmercaptoacetoacetic acid ethyl ester and 8.8 g of 2-amino-3-methylmercaptocrotonic acid ethyl ester in 30 ccs of methanol are heated to the boil overnight and, after cooling, light yellow crystals of melting point 110° C. (ethanol) are obtained, yield: 35%.

EXAMPLE 7

2,6-Dimethylmercaptomethyl-4-(-pyridyl)-1,4-dihydropyridine-3,5-dicarboxylic acid diethyl ester.

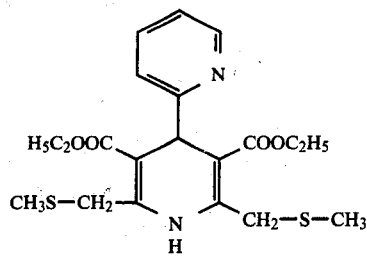

A solution of 5.2 ccs of pyridine-2-aldehyde, 8.8 g of γ-methylmercaptoacetoacetic acid ethyl ester and 8.8 g of γ-amino-β-methylmercaptocrotonic acid ethyl ester in 40 ccs of ethanol is heated to the boil overnight and concentrated and, with the addition of ether and whilst cooling, yellow crystals of melting point 97°–98° C. are obtained. Yield: 30%

EXAMPLE 8

1-Methyl-2,6-dimethylmercaptomethyl-4-phenyl-1,4-dihydropyridine-3,5-dicarboxylic acid diethyl ester

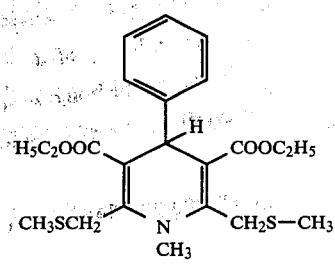

5.3 g of benzaldehyde, 17.6 g of γ-methylmercaptoacetoacetic acid ethyl ester and 4 g of methylamine chlorohydrate in 70 ccs of pyridine are heated to 90°–100° C. for 6 hours and poured into ice-water and the mixture is taken up in ether. The ether solution is washed until free from pyridine, dried over sodium sulphate and evaporated.

Light yellow crystals, from ethanol, of melting point 116°–118° C., yield: 50%.

EXAMPLE 9

2-Methylmercaptomethyl-6-methyl-4--pyridyl-1,4-dihydropyridine-3,5-dicarboxylic acid diethyl ester

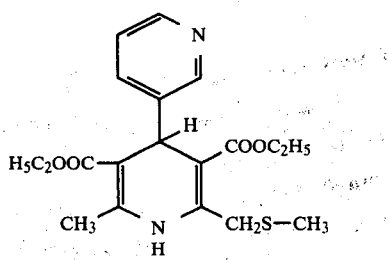

10.70 g of pyridine-3-aldehyde, 17.86 g of γ-methylmercaptoacetoacetic acid ethyl ester and 6.13 g of β- aminocrotonic acid ethyl ester are heated to the boil overnight in 80 ccs of thanol. After cooling, the precipitate is filtered off.

Light yellow crystals of melting point 136° C., yield: 55%.

EXAMPLE 10

2-Methylmercaptomethyl-6-methyl-4--pyridyl-1,4-dihydropyridine-3,4-dicarboxylic acid diethyl ester

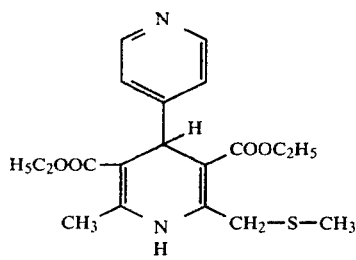

10.7 g of pyridine-4-aldehyde, 17.8 g of γ-methylmercaptoacetoacetic acid ethyl ester and 6.1 g of β-aminocrotonic acid ethyl ester are heated to the boil overnight in 80 ccs of ethanol. After cooling, the precipitate is filtered off.

Light yellow crystals of melting point 146° C., yield: 45%.

EXAMPLE 11

2-Methylmercapto-6-methyl-4-(2'-methoxyphenyl)-1,4-dihydropyridine-3,5-dicarboxylic acid diethyl ester

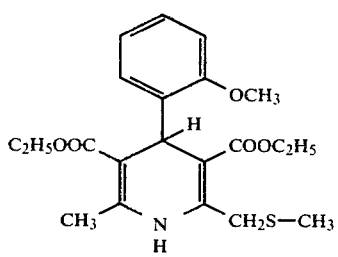

13.6 g of 2-methoxybenzaldehyde, 17.6 g of γ-methylmercaptoacetoacetic acid ethyl ester and 13 g of β-aminocrotonic acid ethyl ester in 80 ccs of ethanol are heated under reflux overnight, the mixture is cooled and the precipitate is filtered off and recrystallised from ethanol.

Yellow crystals of melting point 175° C., yield: 35%

EXAMPLE 12

2-Methylmercapto-6-methyl-4-(3'-cyanophenyl)-1,4-dihydropyridine-3,5-dicarboxylic acid diethyl ester

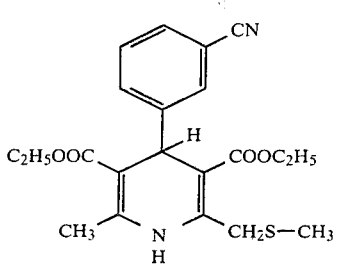

13.9 g of 3-cyanobenzaldehyde, 17.6 g of γ-methylmercaptoacetoacetic acid ethyl ester and 13 g of β-aminocrotonic acid ethyl ester in 80 ccs of ethanol are heated under reflux overnight, the mixture is cooled and the precipitate is filtered off and recrystallised from ethanol.

Yellow crystals of melting point 150° C., yield: 30%.

EXAMPLE 13

2-Acetoxymethyl-6-methyl-4-(3'-nitrophenyl)-1,4-dihydropyridine-3,5-dicarboxylic acid diethyl ester

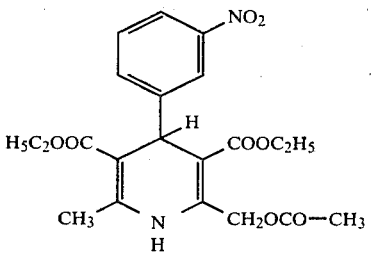

7.5 g of 3-nitrobenzaldehyde, 9.4 g of γ-acetoxyacetoacetic acid ethyl ester and 6.5 g of β-aminocrotonic acid ethyl ester in 40 ccs of ethanol are heated under reflux for 20 hours, the mixture is cooled and the precipitate is filtered off.

Yellow crystals of melting point 106° C., yield: 45%.

EXAMPLE 14

2-Acetoxymethyl-6-methyl-4-(2'-nitrophenyl)-1,4-dihydropyridine-3-carboxylic acid ethyl ester 5-carboxylic acid methyl ester

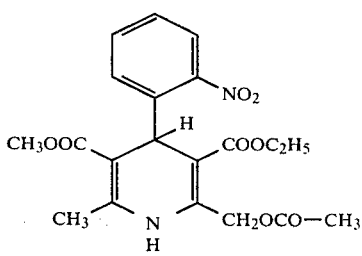

7.5 g of nitro-benzaldehyde, 9.4 g of γ-acetoxyacetoacetic acid ethyl ester and 5.8 g of β-aminocrotonic acid methyl ester are heated to the boil overnight in 40 ccs of ethanol. The mixture is then cooled and the precipitate is filtered off.

Yellow crystals of melting point 116°–118° C., yield: 45%.

EXAMPLE 15

2-Acetoxymethyl-6-methyl-4-(2'-trifluorophenyl)-1,4-dihydropyridine-3,5-dicarboxylic acid diethyl ester

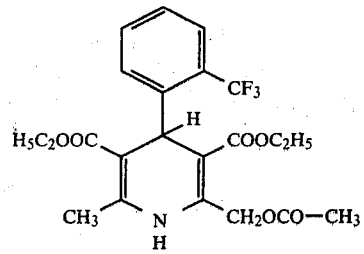

A solution of 8.7 g of 2-trifluoro-benzaldehyde, 9.4 g of γ-acetoxyacetoacetic acid ethyl ester and 6.5 g of β-aminocrotonic acid ethyl ester in 40 ccs of ethanol is heated to the boil overnight and then cooled. After filtering, yellow crystals of melting point 96° C. are obtained, yield: 55%

EXAMPLE 16

2-Acetoxymethyl-6-methyl-4-(-pyridyl)-1,4-dihydropyridine-3,5-dicarboxylic acid diethyl ester

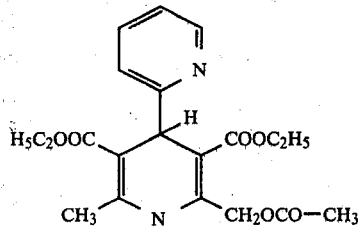

A solution of 5.4 g of pyridine-2-aldehyde, 9.4 g of γ-acetoxyacetoacetic acid ethyl ester and 6.5 g of β-aminocrotonic acid ethyl ester in 40 ccs of ethanol is heated to the boil overnight and then cooled. After filtering, beige crystals of melting point 116° C. are obtained, yield: 60%.

EXAMPLE 17

2-Acetoxymethyl-6-methyl-4-(4'-chlorophenyl)-1,4-dihydropyridine-3,5-dicarboxylic acid diethyl ester

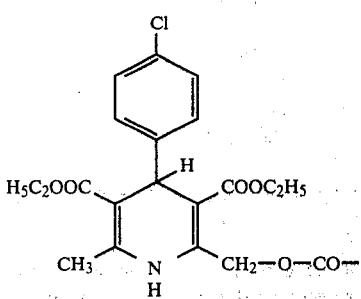

12.6 g of 4-chlorobenzadehydeacetoacetic acid ethyl ester (melting point 86° C.), 9.4 g of γ-acetoxyacetoacetic acid ethyl ester and 5 ccs of ammonia in 30 ccs of methanol are heated to the boil overnight, the mixture is cooled and the precipitate is filtered off.

Light yellow crystals of melting point 116° C., yield 40%.

EXAMPLE 18

2-Acetoxymethyl-6-methyl-4-(2'-methoxyphenyl)-1,4-dihydropyridine-3,5-dicarboxylic acid diethyl ester

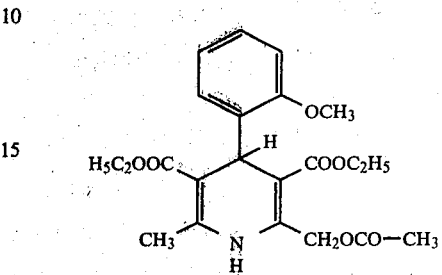

A solution of 6.8 g of 2-methoxy-benzaldehyde, 9.4 g of γ-acetoxyacetoacetic acid ethyl ester and 6.5 g of β-aminocrotonic acid ethyl ester in 40 ccs of ethanol is heated to the boil overnight and then cooled. After filtering, light yellow crystals of melting point 84°–86° C. are obtained.

Yield: 30%

EXAMPLE 19

2-Acetoxymethyl-6-methyl-4-phenyl-1,4-dihydropyridine-3,5-dicarboxylic acid diethyl ester

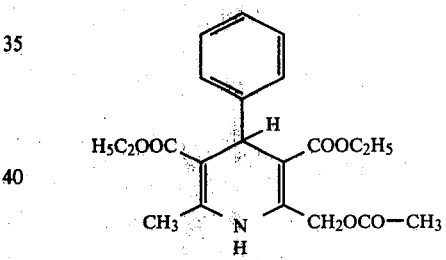

A solution of 5 g of benzaldehyde, 9.4 g of γ-acetoxyacetoacetic acid ethyl ester and 6.5 g of β-aminocrotonic acid ethyl ester in 50 ccs of dioxane is heated to the boil overnight and then cooled. After filtering, light yellow crystals of melting point 104°–106° C. are obtained, yield: 50%.

EXAMPLE 20

2-Acetoxymethyl-6-methyl-4-(3'-chlorophenyl)-1,4-dihydropyridine-3,5-dicarboxylic acid diethyl ester

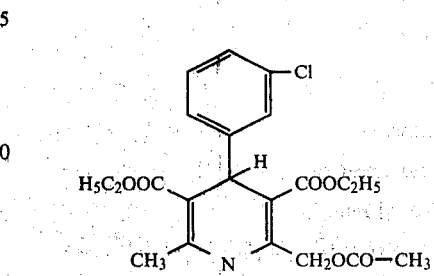

7 g of 3-chlorobenzaldehyde, 9.4 g of γ-acetoxyacetoacetic acid ethyl ester and 6.5 g of β-aminocrotonic acid ethyl ester in 40 ccs of ethanol are heated under reflux for 20 hours, the mixture is cooled and the precipitate is filtered off.

Yellow crystals of melting point 112°–114° C., yield: 65%.

EXAMPLE 21

2-Acetoxymethyl-6-methyl-4-(3'-chlorophenyl)-1,4-dihydropyridine-3-carboxylic acid ethyl ester 5-carboxylic acid methyl ester.

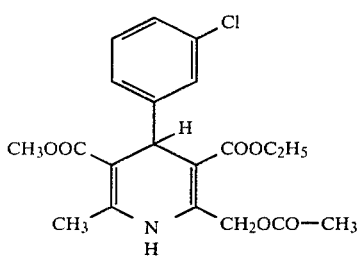

7 g of 3-chlorobenzaldehyde, 9.4 g of γ-acetoxyacetoacetic acid ethyl ester and 5.8 g of β-aminocrotonic acid methyl ester are heated to the boil overnight in 40 ccs of ethanol. Thr mixture is then cooled and filtered.

Light yellow crystals of melting point 106°–108° C., yield: 65%.

EXAMPLE 22

2-Acetoxymethyl-6-methyl-4-(3'-chlorophenyl)-1,4-dihydropyridine-3-carboxylic acid ethyl ester 5-carboxylic acid isopropyl ester

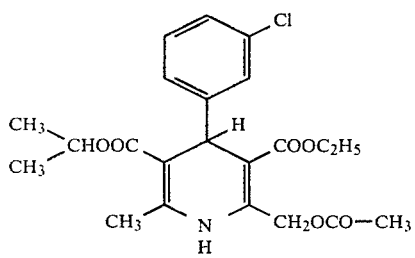

7 g of 3-chlorobenzaldehyde, 9.4 g of γ-acetoxyacetoacetic acid ethyl ester and 7.1 g of β-aminocrotonic acid isopropyl ester in 40 ccs of ethanol are heated to the boil overnight, the mixture is cooled and the precipitate is filtered off.

Light yellow crystals of melting point 120°–122° C., yield: 60%.

EXAMPLE 23

2-Acetoxymethyl-6-methyl-4-(3'-chlorophenyl)-1,4-dihydropyridine-3-carboxylic acid ethyl ester 5-carboxylic acid-methoxyethyl ester

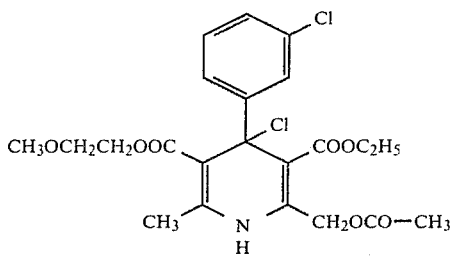

A solution of 7 g of 3-chlorobenzaldehyde, 9.4 g of γ-acetoxyacetoacetic acid ethyl ester and 7.9 g of β-aminocrotonic acid (β-methoxyethyl ester) in 40 ccs of ethanol is heated to the boil overnight and then cooled.

Light yellow crystals of melting point 98°–100° C., yield: 45%.

EXAMPLE 24

2-Acetoxymethyl-6-methyl-4-(3'-chlorophenyl)-1,4-dihydropyridine-3-carboxylic acid ethyl ester 5-carboxylic acid propyl ester

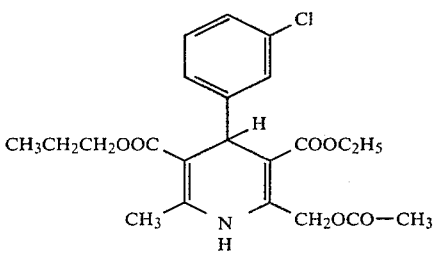

7 g of 3-chlorobenzaldehyde, 9.4 g of γ-acetoxyacetoacetic acid ethyl ester and 7.1 g of β-aminocrotonic acid propyl ester are heated to the boil overnight in 40 ccs of ethanol, the mixture is cooled and the precipitate is then filtered off.

Light yellow crystals of melting point 120°–121° C., yield: 60%

EXAMPLE 25

2-Acetoxymethyl-6-methyl-4-(3'-nitrophenyl)-1,4-dihydropyridine-3-carboxylic acid ethyl ester 5-carboxylic acid-methoxyethyl ester

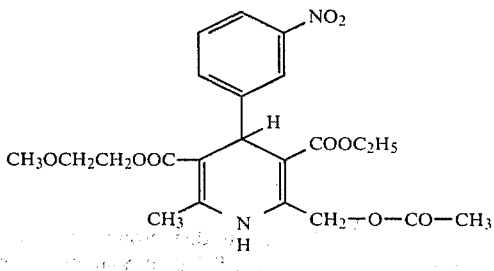

A solution of 7.5 g of 3-nitrobenzaldehyde, 9.4 g of γ-acetoxyacetoacetic acid (β-methoxyethyl)-ester and 7.9 g of β-aminocrotonic acid-(β-methoxyethyl ester) in 40 ccs of ethanol is heated under reflux overnight and cooled and, after filtering, yellow crystals of melting point 106° C. are obtained, yield: 60%.

EXAMPLE 26

2-Acetoxymethyl-6-methyl-4-(3'-nitrophenyl)-4-1,4-dihydropyridine-3-carboxylic acid ethyl ester 5-carboxylic acid propyl ester

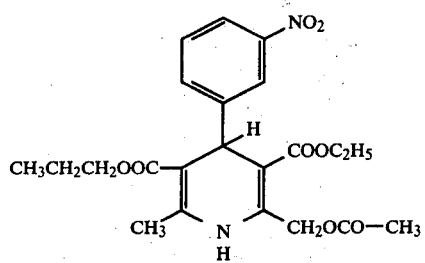

After heating a solution of 7.5 g of 3-nitrobenzaldehyde, 9.4 g of γ-acetoxyacetoacetic acid ethyl ester and 7.1 g β-aminocrotonic acid propyl ester in 40 ccs of ethanol under reflux for 20 hours, light yellow crystals of melting point 118° C. are obtained after cooling, yield: 65%.

EXAMPLE 27

2-Acetoxymethyl-6-methyl-4-(3'-nitrophenyl)-1,4-dihydropyridine-3-carboxylic acid ethyl ester 5-carboxylic acid isopropyl ester

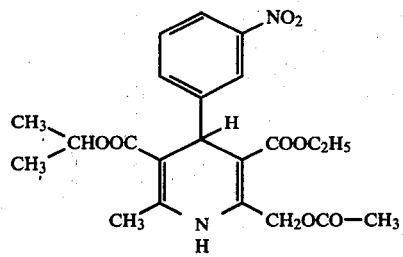

After heating a solution of 7.5 g of 3-nitrobenzaldehyde, 9.4 g of acetoxyacetoacetic acid ethyl ester and 7.1 g of β-aminocrotonic acid isopropyl ester in 40 ccs of ethanol under reflux for 20 hours, yellow crystals of melting point 120°–122° C. are obtained after subsequent cooling, yield: 65%.

EXAMPLE 28

2-Acetoxymethyl-6-methyl-4-pyridyl-1,4-dihydropyridine-3,5-dicarboxylic acid diethyl ester.

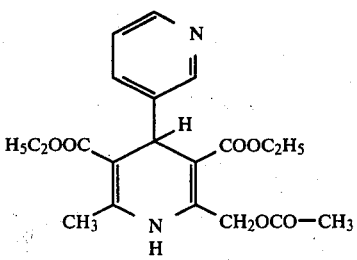

A solution of 5.2 ccs of pyridine-2-aldehyde, 9.4 g of γ-acetoxyacetoacetic acid ethyl ester and 6.5 g of β-aminocrotonic acid ethyl ester in 40 ccs of ethanol is heated to the boil overnight and then cooled. Agter filtering, beige crystals of melting point 122° C. are obtained, yield: 55%.

EXAMPLE 29

2-Acetoxymethyl-6-methyl-4-(2'-chlorophenyl)-1,4-dihydropyridine-3,5-dicarboxylic acid diethyl ester

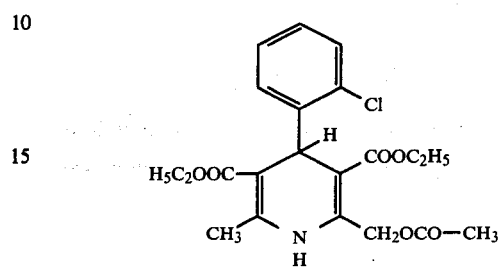

7 g of 2-chlorobenzaldehyde, 9.4 g of γ-acetoxyacetoacetic acid ethyl ester and 6.5 g of β-aminocrotonic acid ethyl ester in 40 ccs of ethanol are heated under reflux overnight and cooled and light yellow crystals of melting point 102° C. are obtained, yield: 40%.

EXAMPLE 30

2-Acetoxymethyl-6-methyl-4-(3'-methoxyphenyl)-1,4-dihydropyridine-3,5-dicarboxylic acid diethyl ester

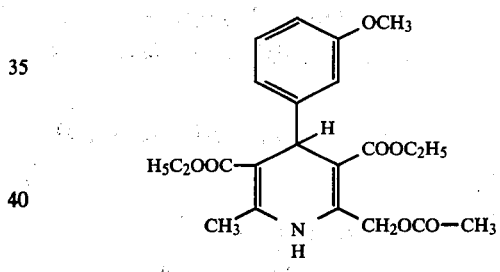

After heating a solution of 6.8 g of 3-methoxybenzaldehyde, 9.4 g of γ-acetoxyacetoacetic acid ethyl ester and 6.5 g of β-aminocrotonic acid ethyl ester in 40 ccs of ethanol for 20 hours, the mixture is cooled and the precipitate is filtered off.

Light yellow crystals of melting point 106° C. are obtained, yield: 40%.

EXAMPLE 31

2-Acetoxymethyl-6-methyl-4-(4'-methoxyphenyl)-1,4-dihydropyridine-3,5-dicarboxylic acid diethyl ester

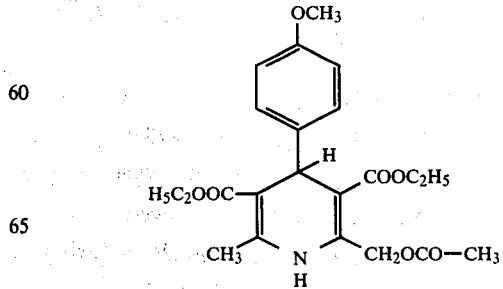

After heating a solution of 5.7 g of 4-methoxybenzaldehyde, 7.9 g of γ-acetoxyacetoacetic acid ethyl ester and 5.5 g of β-aminocrotonic acid ethyl ester in 40 ccs of ethanol for 20 hours, the mixture is cooled and the precipitate is filtered off and recrystallised from ether. White crystals of melting point 89°–90° C., yield: 45%

EXAMPLE 32

2-Acetoxymethyl-6-methyl-4-(3'-fluorophenyl)-1,4-dihydropyridine-3,5-dicarboxylic acid diethyl ester

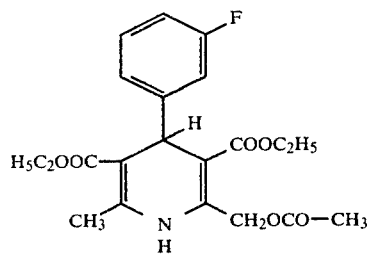

6.3 g of 3-fluorobenzaldehyde, 9.5 g of γ-acetoxyacetoacetic acid ethyl ester and 6.5 g of β-aminocrotonic acid ethyl ester in 40 ccs of ethanol are heated under reflux for 48 hours, the mixture is cooled and the precipitate is filtered off.

Light yellow crystals of melting point 104° C. (ethanol), yield: 60%.

EXAMPLE 33

2,6-Di-(phthalimodomethyl)-4-(3'-chlorophenyl)-1,4-dihydropyridine-3,5-dicarboxylic acid diethyl ester

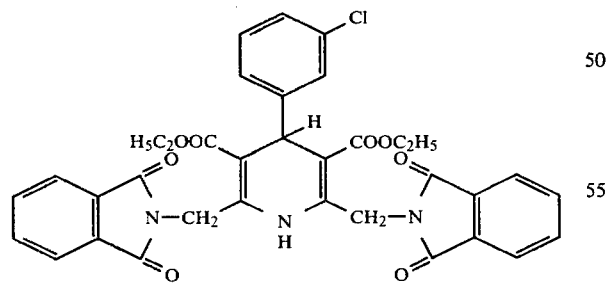

After heating a solution of 7 g of 3-chlorobenzaldehyde, 28 g of γ-phthalimidoacetoacetic acid ethyl ester and 7 ccs of ammonia in 120 ccs of methanol under reflux for 70 hours, the mixture is allowed to cool, whilst stirring, and light yellow crystals of melting point 197°–200° C. are obtained, yield: 55%.

EXAMPLE 34

2-Phthalimidomethyl-6-methyl-4-pyridyl-1,4-dihydropyridine-3,5-dicarboxylic acid diethyl ester

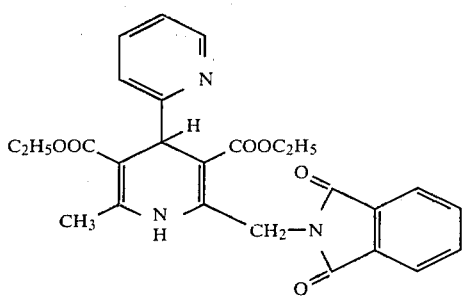

A solution of 4.7 ccs of pyridine-2-aldehyde, 12.4 g of phthalimidoacetoacetic acid ethyl ester and 5.85 g of β-aminocrotonic acid ethyl ester in 100 ccs of ethanol is heated under reflux for 24 hours and, after cooling and filtering, crystals (beige) of melting point 156°–158° C. are obtained, yield: 75%.

EXAMPLE 35

2-Phthalimodomethyl-6-methyl-4-(2'nitrophenyl)-1,4-dihydropyridine-3-carboxylic acid ethyl ester 5-carboxylic acid methyl ester

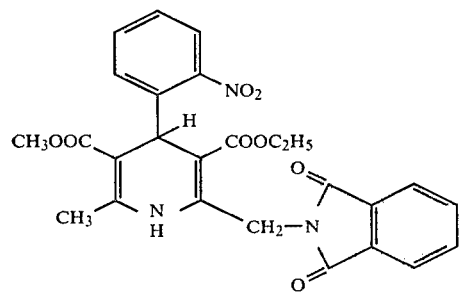

After heating a solution of 7.5 g of 2-nitrobenzaldehyde, 13.8 g of phthalimidoacetoacetic acid ethyl ester and 6 g of β-aminocrotonic acid methyl ester in 100 ccs of ethanol under reflux for 24 hours and subsequent cooling, light yellow crystals of melting point 144°–146° C. are obtained, yield: 55%.

EXAMPLE 36

2-Phthalimidomethyl-6-methyl-4-(2'-trifluoromethylphenyl)-1,4-dihydropyridine-3,5-dicarboxylic acid diethyl ester

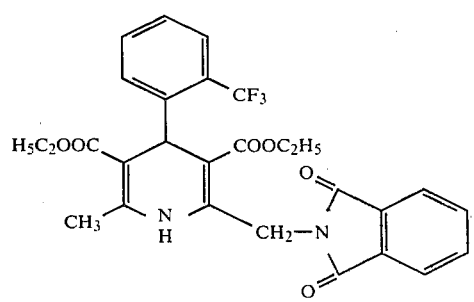

17.4 g of 2-trifluoromethylbenzaldehyde, 28 g of δ-phthalimidoacetoacetic acid ethyl ester and 13 g of β-aminocrotonic acid ethyl ester are heated under reflux overnight in 150 ccs of dioxane. The mixture is then cooled and filtered.

Yellow crystals of melting point 175° C., yield 65%.

EXAMPLE 37

2-Phthalimidomethyl-6-methyl-4-(2'-chlorophenyl)-1,4-dihydropyridine-3,5-dicarboxylic acid diethyl ester

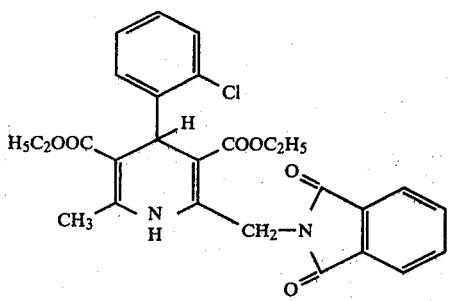

28 g of 2-chlorobenzaldehyde, 56 g of phthalimidoacetoacetic acid ethyl ester and 25.8 g of β-aminocrotonic acid ethyl ester in 250 ccs of ethanol are heated to the boil under reflux for about 70 hours, the mixture is allowed to cool, whilst stirring, and, after filtering, light yellow crystals of melting point 166° C. are obtained, yield: 50%.

EXAMPLE 38

2-Phthalimidomethyl-6-methyl-4-(-pyridyl)-1,4-dihydropyridine-3,5-dicarboxylic acid diethyl ester

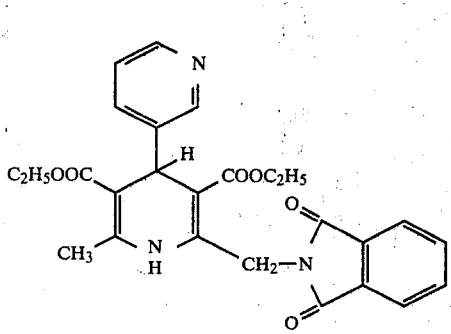

A solution of 4.7 ccs of pyridine-3-aldehyde, 12.4 g of phthalimidoacetoacetic acid ethyl ester and 5.85 g of β-aminocrotonic acid ethyl ester in 100 ccs of ethanol is heated under reflux for 24 hours and, after cooling and filtering, crystals (beige) of melting point 165° C. are obtained, yield: 65%.

EXAMPLE 39

2-Phthalimidomethyl-5-methyl-4-(3'-nitrophenyl)-1,4-dihydropyridine-3-carboxylic acid ethyl ester 5-carboxylic acid methyl ester

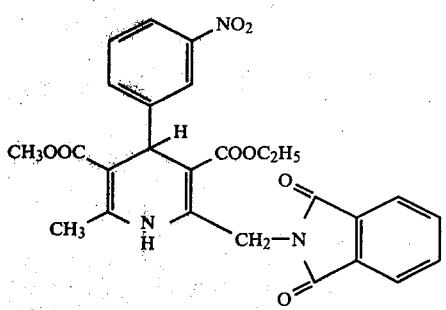

After heating a solution of 7.5 g of 3-nitrobenzaldehyde, 13.8 g of phthalimidoacetoacetic acid ethyl ester and 6 g of β-aminocrotonic acid methyl ester in 100 ccs of n-propanol under reflux for 40 hours and subsequent cooling, light brown crystals of melting point 188°–190° C. are obtained, yield: 65%.

EXAMPLE 40

2-Phthalimidomethyl-6-methyl-4-(phenyl)-1,4-dihydropyridine-3,5-dicarboxylic acid diethyl ester

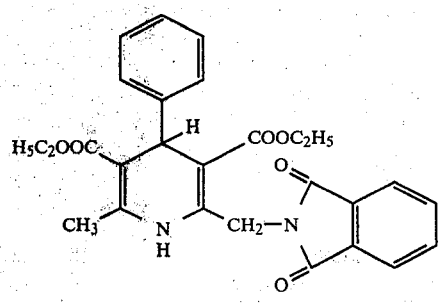

A solution of 10.6 g of benzaldehyde, 28 g of phthalimidoacetoacetic acid ethyl ester and 13 g of β-aminocrotonic acid ethyl ester in 150 ccs of ethanol is heated under reflux for 2×24 hours, the mixture is stirred overnight at room temperature and the precipitate is filtered off and washed with alcohol and ether. Light yellow crystals of melting point 169°–170° C. are obtained in 75% yield.

EXAMPLE 41

2-Phthalimidomethyl-6-methyl-4-(2'-methoxyphenyl)-1,4-dihydropyridine-3-carboxylic acid ethyl ester 5-carboxylic acid methyl ester

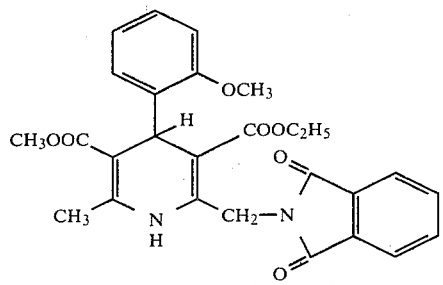

After heating a solution of 6.8 g of 2-methoxybenzaldehyde, 14 g of phthalimidoacetoacetic acid ethyl ester and 6 g of β-aminocrotonic acid methyl ester in 80 ccs of dioxane under reflux for 24 hours and subsequent cooling, light yellow crystals of melting point 92° C. are obtained, yield: 65%.

EXAMPLE 42

2-Phthalimidomethyl-6-methyl-4-(3'-chlorophenyl)-1,4-dihydropyridine-3,5-dicarboxylic acid diethyl ester

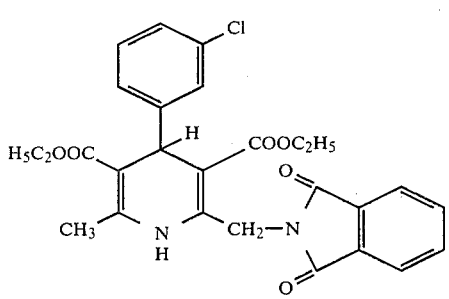

28 g of 3-chlorobenzaldehyde, 56 g of phthalimidoacetoacetic acid ethyl ester and 25.8 g of β-aminocrotonic acid ethyl ester in 250 ccs of ethanol are heated to the boil under reflux for 3×24 hours, the mixture is allowed to cool, whilst stirring, and, after filtering, light yellow crystals of melting point 135°–136° C. are obtained, yield: 55%.

EXAMPLE 43

2-Phthalimidomethyl-6-methyl-4-(2'-methylmercaptophenyl)-1,4-dihydropyridine-3,5-dicarboxylic acid diethyl ester

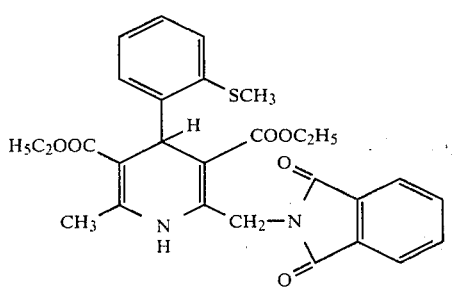

A solution of 10 g of 2-methylmercapto-benzaldehyde (77% pure), 14 g of phthalimidoacetoacetic acid ethyl ester and 6.5 g of β-aminocrotonic acid ethyl ester in 100 ccs of ethanol is heated under reflux for 2×24 hours and, after subsequent cooling, the precipitate is filtered off.

Light yellow crystals, yield: 35%.

EXAMPLE 44

2-Phthalimidomethyl-6-methyl-4-(2'-nitro-3'-methoxyphenyl)-1,4-dihydropyridine-3-carboxylic acid ethyl ester 5-carboxylic acid methyl ester

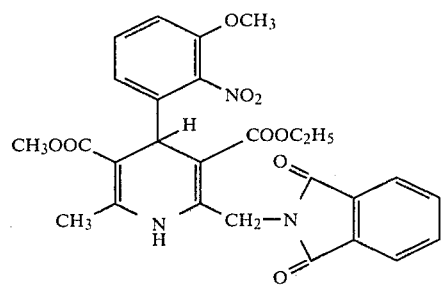

9 g of 2-nitro-3-methoxybenzaldehyde, 14 g of phthalimidoacetoacetic acid ethyl ester and 5.7 g of γ-aminocrotonic acid methyl ester are heated to the boil under reflux for 50 hours, the mixture is then allowed to cool, whilst stirring, and, after filtering, light yellow crystals of melting point 138°–140° C. are obtained, yield: 85%.

EXAMPLE 45

2-Phthalimidomethyl-6-methyl-4-(4'-nitrophenyl)-1,4-dihydropyridine-3,5-dicarboxylic acid diethyl ester

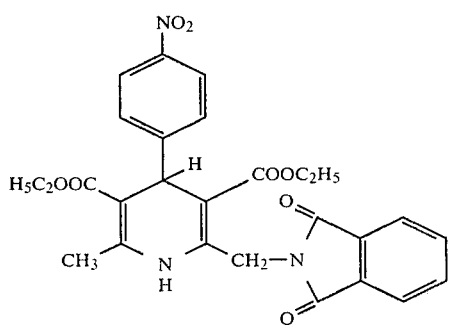

7.5 g of 4-nitrobenzaldehyde, 14 g of γ-phthalimidoacetoacetic acid ethyl ester and 6.5 g of -aminocrotonic acid ethyl ester are heated to the boil for 50 hours in 80 ccs of ethanol.

The mixture is then allowed to cool, whilst stirring, and filtered. Yellow crystals of melting point 152°–155° C., yield: 45%.

EXAMPLE 46

2,6-Di-(phthalimidomethyl)-4-(4'-nitrophenyl)-1,4-dihydropyridine-3,5-dicarboxylic acid diethyl ester

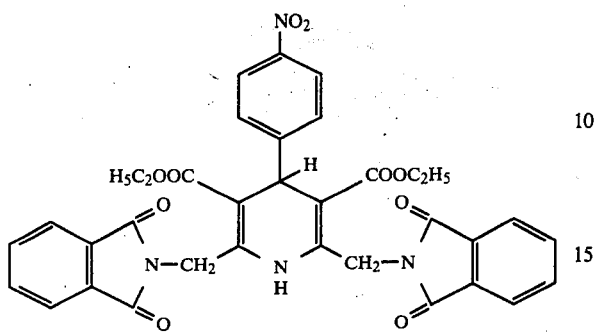

7.5 g of 4-nitrobenzaldehyde, 28 g of γ-phthalimidoacetoacetic acid ethyl ester and 7 ccs of concentrated ammonia in 120 ccs of ethanol are heated to the boil under reflux for 60 hours and the product is filtered off after cooling on ice.

Light yellow crystals of melting point 216°–218° C., yield: 80%.

EXAMPLE 47

2,6-Di-(phthalimidomethyl)-4-(2'-chlorophenyl)-1,4-dihydropyridine-3,5-dicarboxylic acid diethyl ester

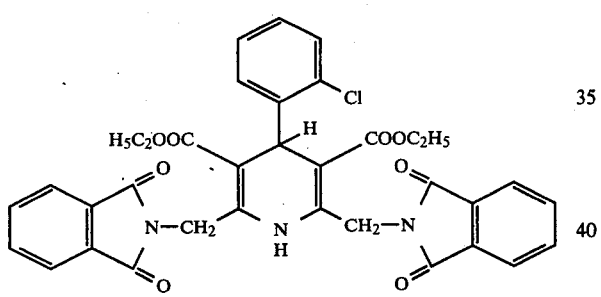

After heating a solution of 7 g of 2-chlorobenzaldehyde, 28 g of γ-phthalimidoacetoacetic acid ethyl ester and 7 ccs of ammonia in 120 ccs of ethanol under reflux for 70 hours, the mixture is allowed to cool, whilst stirring, and light yellow crystals of melting point 162°–164° C. are obtained, yield: 75%.

EXAMPLE 48

2,6-Di-(phthalimidoethyl)-4-(2'-chlorophenyl)-1,4-dihydropyridine-3,5-dicarboxylic acid diethyl ester

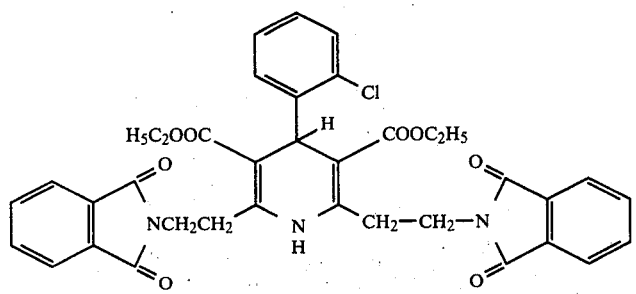

3.5 g of 2-chlorobenzaldehyde, 16 g of δ-phthalimidopropionylacetic acid ethyl ester (melting point 90°) and 6 ccs of ammonia are heated to the boil in 40 ccs of ethanol for 70 hours. After cooling and filtering, yellow crystals of melting point 170° are obtained, yield: 60%.

EXAMPLE 49

2-Phthalimidomethyl-6-methyl-4-(-pyridyl)-1,4-dihydropyridine-3,5-dicarboxylic acid diethyl ester

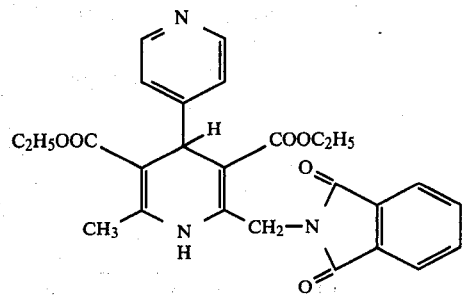

A solution of 5.2 ccs of pyridine-4-aldehyde, 14.0 g of phthalimidoacetoacetic acid ethyl ester and 6.5 g of β-aminocrotonic acid ethyl ester in 80 ccs of ethanol is heated under reflux for 24 hours and, after cooling and filtering, white crystals of melting point 205°–207° C. (ethanol) are obtained, yield: 65%.

EXAMPLE 50

2-Phthalimidomethyl-6-methyl-4-(4'-fluorophenyl)-1,4-dihydropyridine-3,5-dicarboxylic acid diethyl ester

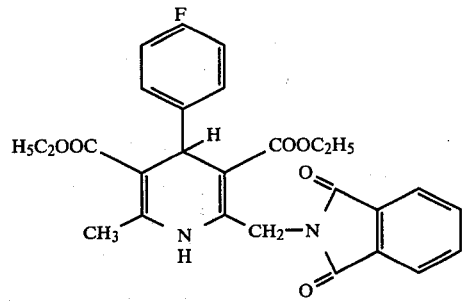

12.4 g of 4-fluorobenzaldehyde, 31 g of phthalimidoacetic acid ethyl ester and 13 g of β-aminocrotonic acid ethyl ester in 100 ccs of ethanol are heated to the boil under reflux for 2×24 hours, the mixture is allowed to cool, whilst stirring, and, after filtering, yellow crystals of melting point 144°–145° C. (ethanol) are obtained, yield: 80%.

EXAMPLE 51

2,6-Di-(phthalimidomethyl)-4-(4'-nitrophenyl)-1,4-dihydropyridine-3,5-dicarboxylic acid diethyl ester

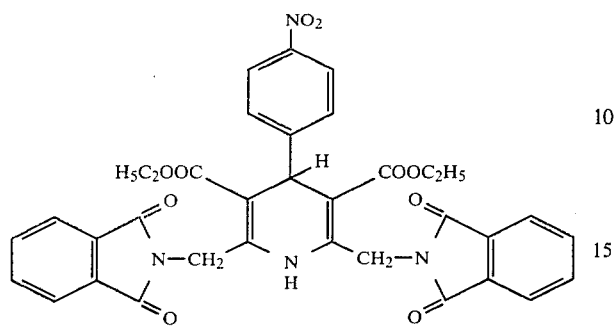

7.5 g of 4-nitrobenzaldehyde, 28 g of γ-phthalimidoacetoacetic acid ethyl ester and 7 ccs of concentrated ammonia in 120 ccs of ethanol are heated to the boil under reflux for 60 hours and the product is filtered off after cooling on ice.

Light yellow crystals of melting point 216°–218° C., yield: 80%.

EXAMPLE 52

2-Methylthiomethyl-6-methyl-4-(3-nitrophenyl)-5-methylsulphonyl-1,4-dihydropyridine-3-carboxylic acid ethyl ester

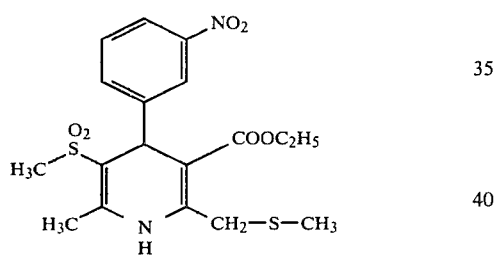

The compound was obtained by heating 15.1 g of 3-nitrobenzaldehyde, 13.6 g of methylsulphonylacetone and 17.5 g of β-amino-γ-methylthiocrotonic acid ethyl ester in 100 ml of ethanol for 2 hours.

EXAMPLE 53

2-Methylthiomethyl-6-methyl-4-(3-nitrophenyl)-5-phenylsulphonyl-1,4-dihydropyridine-3-carboxylic acid ethyl ester

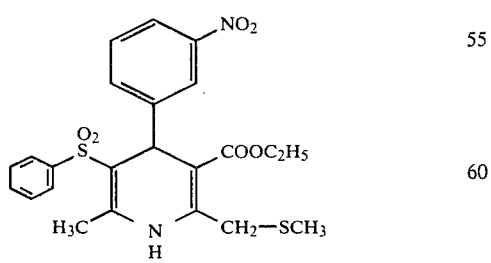

The compound was obtained by heating 15.1 g of 3-nitrobenzaldehyde, 19.8 g of phenylsulphonylacetone and 17.5 g of β-aminoγ-methylthiocrotonic acid ethyl ester in 100 ml of ethanol for 20 hours.

EXAMPLE 54

2-Phthalimidomethyl-6-methyl-4-(2'-chlorophenyl)-1,4-dihydropyridine-3,5-dicarboxylic acid diethyl ester

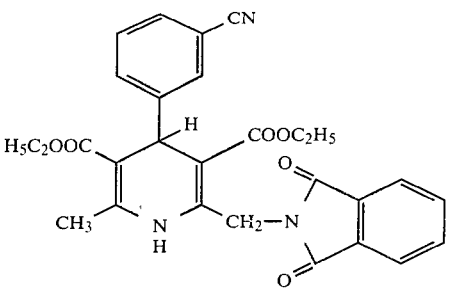

13 g of 2-chlorobenzaldehyde, 28 g of phthalimidoacetoacetic acid ethyl ester and 13 g of β-aminocrotonic acid ethyl ester in 250 ccs of ethanol are heated to the boil under reflux for about 70 hours, the mixture is allowed to cool, whilst stirring, and after filtering, light yellow crystals of melting point 174°–176° C. are obtained; yield: 90%.

EXAMPLE 55

2-Phthalimidomethyl-5-methyl-4-(3'-chlorophenyl)-1,4-dihydropyridine-3-carboxylic acid ethyl ester 5-carboxylic acid methyl ester

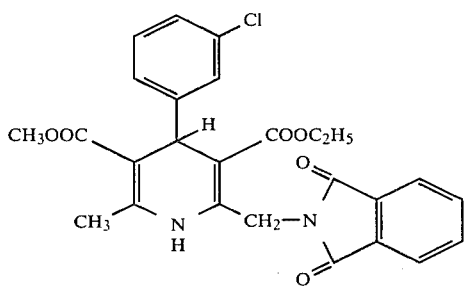

After heating a solution of 14 g of 3-chlorobenzaldehyde, 26 g of phthalimidoacetoacetic acid ethyl ester and 11.5 g of β-aminocrotonic acid methyl ester in 200 ccs of ethanol under reflux for 40 hours and subsequent cooling, light brown crystals of melting point 138°–140° C. are obtained; yield: 65%.

What is claimed is:

1. A 1,4-Dihydropyridine derivative of the formula (I)

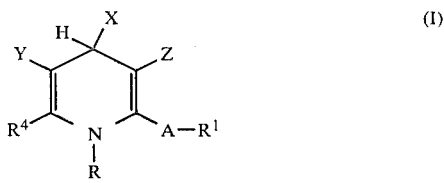

or a pharmaceutically acceptable acid addition salt thereof, in which

R represents hydrogen, alkyl with 1 to 4 carbon atoms, or benzyl, A represents a straight-chain or branched alkylene radical with 1 to 6 carbon atoms, $R^1$ represents a phthalimido radical, Y and Z individually represent the grouping $COOR^2$ wherein $R^2$ represents alkyl, alkenyl, alkinyl, alkoxyalkyl, hydroxyalkyl, alkylmercaptoalkyl, aminoalkyl monoalkylaminoalkyl or dialkylaminoalkyl, the alkyl groups mentioned containing 1 to 6 carbon atoms and the alkenyl and alkinyl groups mentioned containing 2 to 4 carbon atoms, or represents phenyl or benzyl, $R^4$ represents hydrogen, alkyl or alkoxyalkyl with 1 to 4 carbon atoms, or represents the radical $A-R^1$, wherein A and $R^1$ have the above-mentioned meaning, and X represents a phenyl radical which is optionally substituted by one or two identical or different substituents, selected from nitro, halogen, trifluoromethyl, cyano, phenyl, trifluoromethoxy, amino, alkylamino, alkyl, alkoxy or alkylmercapto with 1 or 2 carbon atoms in the alkyl radical in each case, or represents a naphthyl, pyridyl, thienyl, or benzyl radical which is unsubstituted or substituted by nitro or halogen.

2. A compound of claim 1 which is 2,6-Di-(phthalimodomethyl)-4-(3'-chlorophenyl)-1,4-dihydropyridine-3,5-dicarboxylic acid diethyl ester.

3. A compound of claim 1 which is 2-Phthalimidomethyl-6-methyl-4-(2'-chlorophenyl)-1,4-dihydropyridine-3,5-dicarboxylic acid diethyl ester.

4. A compound of claim 1 which is 2-Phthalimidomethyl-6-methyl-4-(-pyridyl)-1,4-dihydropyridine-3,5-dicarboxylic acid diethyl ester.

5. A compound of claim 1 which is 2-Phthalimidomethyl-6-methyl-4-(2'-methoxyphenyl)-1,4-dihydropyridine-3-carboxylic acid ethyl ester 5-carboxylic acid methyl ester.

6. A pharmaceutical composition containing as an active ingredient an effective amount for combating circulatory diseases relating to heart action and blood pressure of a compound according to claim 1 in admixture with a solid or liquefied gaseous diluent or in admixture with a liquid diluent other than a solvent of a molecular weight less than 200 except in the presence of a surface-active agent.

7. A pharmaceutical composition containing as an active ingredient an effective amount for combating circulatory diseases relating to heart action and blood pressure of a compound according to claim 1 in the form of a sterile or isotonic aqueous solution.

8. A composition according to claim 6 containing from 0.5 to 95% by weight of the said active ingredient.

9. A medicament in dosage unit form comprising an effective amount for combating circulatory diseases relating to hear action and blood pressure of a compound according to claim 1 together with an inert pharmaceutical carrier.

10. A medicament of claim 9 in the form of tablets, pills, dragees, capsules, ampoules, or suppositories.

11. A method of combating circulatory diseases in warm blooded animals in need of such treatment orally or parenterally which comprises administering to the animals an amount effective for combating circulatory diseases relating to heart action and blood pressure an active compound according to claim 1 either alone or in admixture with a diluent or in the form of a medicament.

12. A method according to claim 11 in which the active compound is administered in an amount from 0.01 to 100 mg per kg body weight per day.

13. A method according to claim 12 in which the active compound is administered orally or intravenously.

* * * * *